(12) United States Patent
Barnard et al.

(10) Patent No.: US 9,512,422 B2
(45) Date of Patent: *Dec. 6, 2016

(54) GEL PATTERNED SURFACES

(71) Applicant: Illumina, Inc., San Diego, CA (US)

(72) Inventors: Steven M. Barnard, San Diego, CA (US); M. Shane Bowen, San Diego, CA (US); Maria Candelaria Rogert Bacigalupo, San Diego, CA (US); Wayne N. George, Cambridge (GB); Andrew A. Brown, Cambridge (GB); James Tsay, San Diego, CA (US)

(73) Assignee: Illumina, Inc., San Diego, CA (US)

(*) Notice: Subject to any disclaimer, the term of this patent is extended or adjusted under 35 U.S.C. 154(b) by 40 days.

This patent is subject to a terminal disclaimer.

(21) Appl. No.: 13/787,396

(22) Filed: Mar. 6, 2013

(65) Prior Publication Data
US 2014/0243224 A1    Aug. 28, 2014

Related U.S. Application Data

(60) Provisional application No. 61/769,289, filed on Feb. 26, 2013.

(51) Int. Cl.
C12N 15/10 (2006.01)
C12Q 1/68 (2006.01)
B01J 19/00 (2006.01)

(52) U.S. Cl.
CPC ........ *C12N 15/1068* (2013.01); *B01J 19/0046* (2013.01); *C12Q 1/6837* (2013.01);
(Continued)

(58) Field of Classification Search
CPC .............. C12N 15/1068; C12Q 1/6837; C12Q 2563/159; B01J 19/0046
(Continued)

(56) References Cited

U.S. PATENT DOCUMENTS 5,130,238 A   7/1992   Malek
5,223,414 A   6/1993   Zarling et al.
(Continued)

FOREIGN PATENT DOCUMENTS

WO   91/06678   5/1991
WO   00/46408   8/2000
(Continued)

OTHER PUBLICATIONS

Cho et al., JACS, Jan. 26, 2005, 127, pp. 2022-2023.*
(Continued)

*Primary Examiner* — Larry Riggs
*Assistant Examiner* — Karla Dines
(74) *Attorney, Agent, or Firm* — Illumina, Inc.

(57) ABSTRACT

Provided is an array including a solid support having a surface, the surface having a plurality of wells, the wells containing a gel material, the wells being separated from each other by interstitial regions on the surface, the interstitial regions segregating the gel material in each of the wells from the gel material in other wells of the plurality; and a library of target nucleic acids in the gel material, wherein the gel material in each of the wells comprises a single species of the target nucleic acids of the library. Methods for making and using the array are also provided.

25 Claims, 11 Drawing Sheets

(52) U.S. Cl.
CPC ........... *B01J 2219/00317* (2013.01); *B01J 2219/00621* (2013.01); *B01J 2219/00644* (2013.01); *B01J 2219/00722* (2013.01)

(58) Field of Classification Search
USPC .......................................................... 506/9
See application file for complete search history.

(56) References Cited

U.S. PATENT DOCUMENTS

| | | | |
|---|---|---|---|
| 5,455,166 | A | 10/1995 | Walker |
| 5,641,658 | A | 6/1997 | Adams et al. |
| 6,214,587 | B1 | 4/2001 | Dattagupta |
| 6,355,431 | B1 | 3/2002 | Chee et al. |
| 6,372,813 | B1 * | 4/2002 | Johnson ........... G01N 33/54353 435/174 |
| 6,692,915 | B1 * | 2/2004 | Nallur .................. C12Q 1/6874 435/173.1 |
| 6,699,693 | B1 | 3/2004 | Marians et al. |
| 6,890,741 | B2 | 5/2005 | Fan et al. |
| 6,913,884 | B2 | 7/2005 | Stuelpnagel et al. |
| 6,929,915 | B2 | 8/2005 | Benkovic et al. |
| 7,057,026 | B2 | 6/2006 | Barnes et al. |
| 7,115,400 | B1 | 10/2006 | Adessi et al. |
| 7,211,414 | B2 | 5/2007 | Hardin et al. |
| 7,315,019 | B2 | 1/2008 | Turner et al. |
| 7,329,492 | B2 | 2/2008 | Hardin et al. |
| 7,399,590 | B2 | 7/2008 | Piepenburg et al. |
| 7,405,281 | B2 | 7/2008 | Xu et al. |
| 7,582,420 | B2 | 9/2009 | Oliphant et al. |
| 7,687,103 | B2 * | 3/2010 | Light et al. ...................... 427/58 |
| 7,785,790 | B1 | 8/2010 | Church et al. |
| 8,017,339 | B2 | 9/2011 | Piepenburg et al. |
| 8,062,850 | B2 | 11/2011 | Piepenburg |
| 8,071,308 | B2 | 12/2011 | Piepenburg et al. |
| 2002/0055100 | A1 | 5/2002 | Kawashima et al. |
| 2004/0002090 | A1 | 1/2004 | Mayer et al. |
| 2004/0096853 | A1 | 5/2004 | Mayer |
| 2004/0248213 | A1 * | 12/2004 | Karlsson ............ G01N 33/5005 435/7.2 |
| 2005/0053980 | A1 | 3/2005 | Gunderson et al. |
| 2005/0064460 | A1 | 3/2005 | Holliger et al. |
| 2005/0100951 | A1 * | 5/2005 | Pircher .............. 435/6 |
| 2005/0130173 | A1 | 6/2005 | Leamon et al. |
| 2005/0181440 | A1 | 8/2005 | Chee et al. |
| 2007/0099208 | A1 | 5/2007 | Drmanac et al. |
| 2007/0128624 | A1 | 6/2007 | Gormley et al. |
| 2008/0009420 | A1 | 1/2008 | Schroth et al. |
| 2008/0108082 | A1 | 5/2008 | Rank et al. |
| 2008/0241836 | A1 * | 10/2008 | Zainiev et al. .................. 435/6 |
| 2009/0032401 | A1 | 2/2009 | Ronaghi et al. |
| 2009/0062132 | A1 * | 3/2009 | Borner .............. 506/7 |
| 2009/0186349 | A1 | 7/2009 | Gunderson et al. |
| 2009/0298712 | A1 * | 12/2009 | Kiryukhin et al. ............. 506/16 |
| 2009/0325262 | A1 * | 12/2009 | Hodneland et al. .......... 435/176 |
| 2010/0015607 | A1 * | 1/2010 | Geiss .................. C12Q 1/6876 435/6.11 |
| 2010/0022412 | A1 * | 1/2010 | Rigatti ................. C12Q 1/6837 506/17 |
| 2010/0111768 | A1 | 5/2010 | Banerjee et al. |
| 2010/0304982 | A1 | 12/2010 | Hinz et al. |
| 2011/0059865 | A1 | 3/2011 | Smith et al. |
| 2011/0256186 | A1 * | 10/2011 | Font Perez ......... A61L 27/3604 424/400 |
| 2011/0287951 | A1 * | 11/2011 | Emmert-Buck et al. ......... 506/7 |
| 2012/0045368 | A1 * | 2/2012 | Hinz et al. ...................... 422/69 |
| 2012/0270305 | A1 | 10/2012 | Reed et al. |
| 2012/0316086 | A1 | 12/2012 | Lin et al. |
| 2013/0116153 | A1 | 5/2013 | Bowen et al. |
| 2013/0338042 | A1 | 12/2013 | Shen et al. |
| 2014/0079923 | A1 | 3/2014 | George et al. |

FOREIGN PATENT DOCUMENTS

| | | |
|---|---|---|
| WO | 2004/018497 | 3/2004 |
| WO | 2005/010145 | 2/2005 |
| WO | 2005/065814 | 7/2005 |
| WO | 2006/138257 | 12/2006 |
| WO | 2007/123744 | 11/2007 |
| WO | 2008/093098 | 8/2008 |
| WO | 2012/106072 | 8/2012 |
| WO | 2012/170936 | 12/2012 |
| WO | 2013/063382 | 5/2013 |

OTHER PUBLICATIONS

Oh et al., OMICS, A Journal of Integrative Biology, vol. 10, No. 3, 2006, pp. 327-343.*

Beaucage, S., Current Medicinal Chemistry, 2001, 8, pp. 1213-1244.*

Jackman et al., Analytical Chemistry, 1998, 70, pp. 2280-2287.*

Barsky et al. (Molecular Biology, 2002, vol. 36, No. 4, pp. 437-455).*

Bentley, et al., "Accurate whole human genome sequencing using reversible terminator chemistry", Nature, vol. 456, No. 7218, Nov. 6, 2008, 53-59.

Bleuit, et al., "Mediator proteins orchestrate enzyme-ssDNA assembly during T4 recombination-dependent DNA replication and repair", PNAS 98, 2001, 8298-8305.

Caulfield, et al., "Degradation on polyacrylamides. Part I. Linear polyacrylamide", Polymer 44, 2003, 1331-1337.

Caulfield, et al., "Some Aspects of the Properties and Degradation of Polyacrylamides", Chem Rev 102, 2002, 3067-3083.

Dean, "Comprehensive human genome amplification using multiple displacement amplification", PNAS, 99, 2002, 5261-5266.

Dressman, et al., "Transforming single DNA molecules into fluorescent magnetic particles for detection and enumeration of genetic variations", PNAS, 100(15), 2003, 8817-8822.

Fixe, et al., "Electric-field assisted immobilization and hybridization of DNA oligomers on thin-film microchips", Institute of Physics Publishing, Nanotechnology 16, (2005), 2061-2071.

Hsiao, et al., "Electric-Field-Directed Self-Assembly of Active Enzyme-Nanoparticle Structures", Journal of Biomedicine and Biotechnology vol. 2012, Article ID 178487, Oct. 13, 2011, 9 pages.

Kurenkov, "Degradation of Polyacrylamide and Its Derivaties in Aqueous Solutions", Russian Journal of Applied Chemistry, 75, 2002, 1039-1050.

Lage, Jose M. et al., "Whole genome analysis of genetic alterations in small DNA samples using hyperbranched strand displacement amplification and array-CGH", Genome Research, vol. 13., Issue 2, Feb., Feb. 2003, 294-307.

Lizard!, "Mutation detection and single-molecule counting using isothermal rolling-circle amplification", Nature Genetics, vol. 19, 1998, 225-232.

Morrical, et al., "Amplification of snap-back DNA synthesis reactions by the uvsX recombinase of bacteriophage T4.", JBC 266, 1991, 14031-14038.

Rybenkov, et al., "Probability of DNA knotting and the effective diameter of the DNA double helix", PNAS 90, 1993, 5307-5311.

Sobel, et al., "Effects of Na+ on the persistence length and excluded volume of T7 bacteriophage DNA", Biopolymers, 31, 1991, 1559-1564.

Thornton, "High Rate Thick Film Growth", Annu. Rev. Mater. Sci., 7, 1977, 239-260.

Walker, et al., "Strand displacement amplification--an isothermal, in vitro DNA amplification technique", NAR, 20, 1992, 1691-1696.

Zimmerman, et al., "Estimation of macromolecule concentrations and excluded volume effects for the cytoplasm of *Escherichia coli*", J. Mol. Biol. 222, 1991, 599-620.

* cited by examiner

FIG. 5A
FIG. 5B
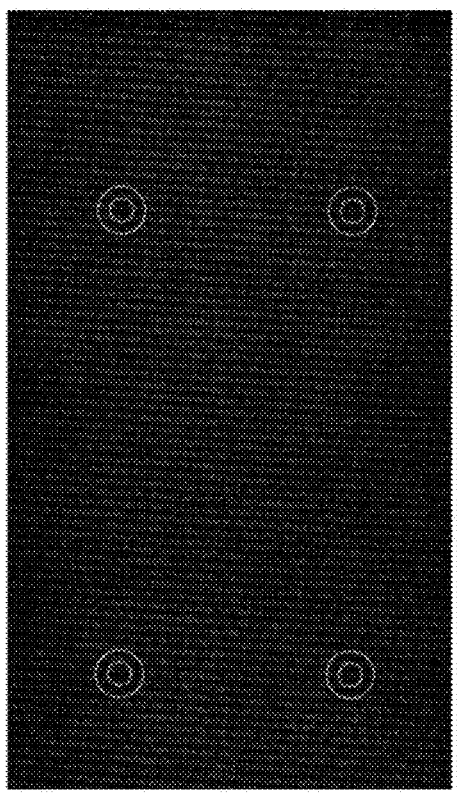
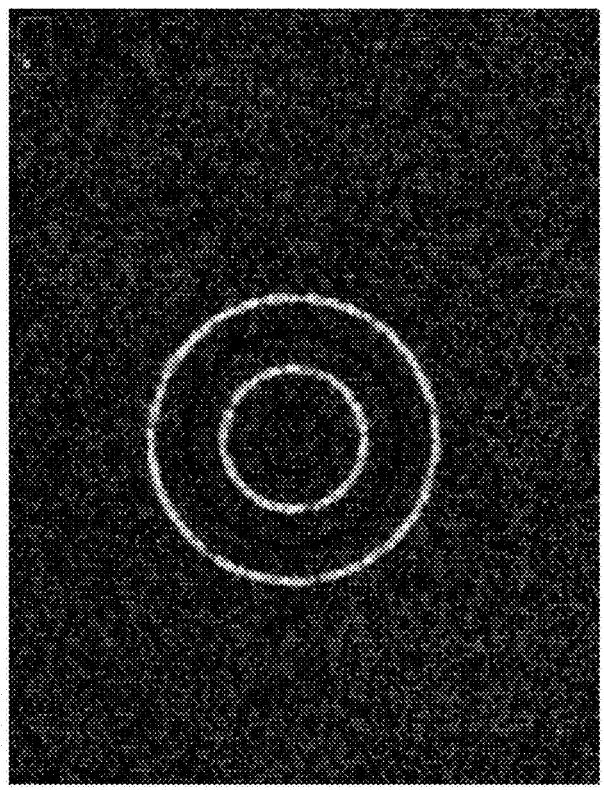

| Lane | Tile | Error Rate | Density (K/mm2) | Density PF (K/mm2) | % Aligned R1 | % Phasing R1 | % Prephasing R1 | %PF | Frac Occupied | Frac Clonal | Percent PadHop |
|---|---|---|---|---|---|---|---|---|---|---|---|
| 5 | 2113 | 0.113 | 1561.6 | 1353.1 | 96.3 | 0.185 | 0.385 | 86.4 | | | |
| 5 | 2105 | 0.146 | 1347.1 | 1121 | 98.7 | 0.263 | 0.433 | 83.2 | | | |
| 5 | 2197 | 0.119 | 1531.4 | 1306.8 | 98.8 | 0.197 | 0.312 | 85.3 | 0.7488 | 0.8419 | 0.0139 |

GEL PATTERNED SURFACES

This application is based on, and claims the benefit of, U.S. Provisional Application No. 61/769,289, filed Feb. 26, 2013, which is incorporated herein by reference.

BACKGROUND

The present disclosure relates generally to solid-phase analytical chemistry, and has specific applicability to nucleic acid arrays for high throughput genomics analysis. The task of cataloguing human genetic variation and correlating this variation with susceptibility to disease stands to benefit from advances in genome wide sequencing methodologies. This cataloguing effort holds promise for identifying the markers in each person's genome that will help medical professionals determine susceptibility of that person to disease, responsiveness to specific therapies such as prescription drugs, susceptibility to dangerous drug side effects and other medically actionable characteristics. The cataloguing effort is well under way. This is due in large part to commercially available genome sequencing methodologies which are sufficiently cost effective to allow test subjects to be evaluated in a research setting. Improvements in sequencing methodologies are needed to accelerate the cataloguing effort. Moreover, the relatively high cost of sequencing has hindered the technology from moving beyond the research centers and into the clinic where doctors can obtain sequences for patients in the general population.

Sequencing methodologies and the systems used to carry them out, exploit a complex collection of technologies. Improvements in some of these technologies have been shown to provide substantial cost reductions. However, it is difficult to predict which if any is amenable to cost reducing improvements. Given the dependencies between the technologies in the sequencing systems it is even more difficult to predict which can be modified without having an adverse impact on the overall performance of the methodology or system. Thus, there exists a need to identify improvements that can bring the promise of genomics research to the clinic where lives can be improved and in many cases saved. The present invention satisfies this need and provides related advantages as well.

BRIEF SUMMARY

The present disclosure provides an array including a solid support having a surface, the surface having a plurality of wells, the wells containing a gel material, the wells being separated from each other by interstitial regions on the surface, the interstitial regions segregating the gel material in each of the wells from the gel material in other wells of the plurality; and a library of target nucleic acids in the gel material, wherein the gel material in each of the wells comprises a single species of the target nucleic acids of the library.

In some embodiments the substrate is configured as an array of wells and the analytes are nucleic acids. Accordingly, this disclosure provides an array that includes a solid support having a surface, the surface having a plurality of wells, the wells containing a gel material, the wells being separated from each other by interstitial regions on the surface, the interstitial regions segregating the gel material in each of the wells from the gel material in other wells of the plurality; and a library of target nucleic acids in the gel material, wherein the gel material in each of the wells includes a single species of the target nucleic acids of the library.

The present disclosure also provides a method of making a substrate. The method can include the steps of (a) providing a solid support having a planar surface, wherein the planar surface is interrupted by one or more concave features and wherein the one or more concave features are bordered by one or more interstitial regions on the planar surface; (b) coating at least a portion of the solid support with a gel material, wherein the portion includes at least one of the concave features and at least one of the interstitial regions; and (c) polishing the planar surface to remove the gel material from the at least one interstitial regions and to maintain the gel material in the at least one concave feature.

Also provided is a method of making a substrate that includes the steps of (a) providing a solid support having a planar surface, wherein the planar surface is interrupted by one or more concave features and wherein the one or more concave features are bordered by one or more interstitial regions on the planar surface; (b) coating at least a portion of the solid support with a gel material, wherein the portion includes at least one of the concave features and at least one of the interstitial regions, wherein the gel material is bound to a probe or capable of binding to a probe; and (c) polishing the planar surface to remove or inactivate the gel material at the at least one interstitial regions, whereby the at least one concave feature retains the gel material that is bound to a probe or capable of binding to a probe and whereby the at least one interstitial regions is not bound to the probe and is not capable of binding to the probe.

A method of making an array can include the steps of (a) providing a solid support having a surface with a plurality of wells, the wells containing a gel material, the wells being separated from each other by interstitial regions on the surface, the interstitial regions segregating the gel material in each of the wells from the gel material in other wells of the plurality; (b) delivering a library of target nucleic acids to the wells of the solid support to produce an array of wells that have a single species of target nucleic acid attached to the gel material in each well, wherein different wells in the array have different target nucleic acid species from the library; and (c) amplifying the target nucleic acids attached to the gel material in the wells of the array to produce a clonal population of an individual target nucleic acid at each of the wells of the array.

This disclosure further provides a method of detecting analytes. The method can include the steps of (a) providing a solid support having a planar surface, wherein the planar surface is interrupted by one or more concave features, wherein the concave features contain gel material, wherein the one or more concave features are bordered by one or more interstitial regions on the planar surface, the interstitial regions being substantially devoid of the gel material, and wherein the gel material is attached to or contains target analytes; (b) contacting the solid support with probes under conditions wherein the target analytes interact specifically with the probes; and (c) detecting the solid support to distinguish at least a subset of the target analytes that interact with one or more of the probes.

In particular embodiments nucleic acids are the analytes that are detected and the concave features are wells. For example a method of detecting nucleic acids can include the steps of (a) providing a solid support having a surface and a library of nucleic acids, the surface having a plurality of wells, the wells containing a gel material, the wells being separated from each other by interstitial regions on the surface, the interstitial regions segregating the gel material in each of the wells from the gel material in other wells of the plurality, a single species of the target nucleic acids of the library being attached to the gel material in each of the wells; (b) contacting the solid support with at least one probe that binds to the target nucleic acids; and (c) detecting the solid support to distinguish the wells having a target nucleic acid species that binds to the at least one probe.

The compositions, apparatus, and methods of the present disclosure are exemplified herein with regard to gel material. It will be understood that the gel material is exemplary and can be replaced with other organic materials including, for example, polymers that may form a surface coating and may not necessarily be considered as gels, per se. Methods set forth herein for applying gel material to a surface, removing the gel material from interstitial regions, attaching analytes to the gel material, using the resulting arrays in analytical or preparative methods etc., can be readily adapted by replacing the gel material with non-gel materials.

BRIEF DESCRIPTION OF THE DRAWINGS

FIG. 2A: bright field images obtained before polishing. FIG. 2B and FIG. 2C: fluorescent images obtained after polishing and hybridization to fluorescently labeled oligonucleotides.

FIG. 5A and FIG. 5B show a multi-color image merge obtained from a HiSeq sequencing cycle of a 1.5 µm pitch nanowell substrate having patterned clusters. FIG. 5A: image showing a field of clusters patterned in gel-containing wells along with four bulls-eye fiducials. FIG. 5B: a higher resolution image showing the mixture of colors (due to a mixed population of amplicons) in a single bulls-eye fiducial.

DETAILED DESCRIPTION

This disclosure provides structured substrates, methods for making structured substrates and methods for using structured substrates. In particular embodiments the substrates include a solid support having concave regions, such as wells, that contain gel material (e.g. being coated by the gel material). The gel material can in turn be attached to an analyte of interest, such as a nucleic acid. In particular embodiments the gel-containing regions are discrete, being separated by interstitial regions that lack the ability to attach the analyte of interest. For example, the interstitial regions may lack the gel material. Alternatively, the gel material in the interstitial regions may be inactivated or otherwise modified to lack an activity or characteristic of the gel material in the concave regions, such as the ability to support analyte attachment. The resulting segregation of the gel regions provides advantages when carrying out reactions on the analytes and/or detecting the analytes. An exemplary advantage can be demonstrated in the instance of an array of target nucleic acids distributed among gel-containing wells. Here, an amplification reaction can be carried out on the structured substrate using the nucleic acids as templates to form nucleic acid colonies that grow in or on the gel (e.g. nucleic acid features of the array). The interstitial regions function to confine the area of growth for the colony. The individual features of the resulting array can be distinguished with relative ease due to the discrete pattern created by the gel-containing wells. The pattern can also provide benefits of increasing the density of features and reducing processing requirements for image registration as compared to random arrays of nucleic acids.

Figure 1:
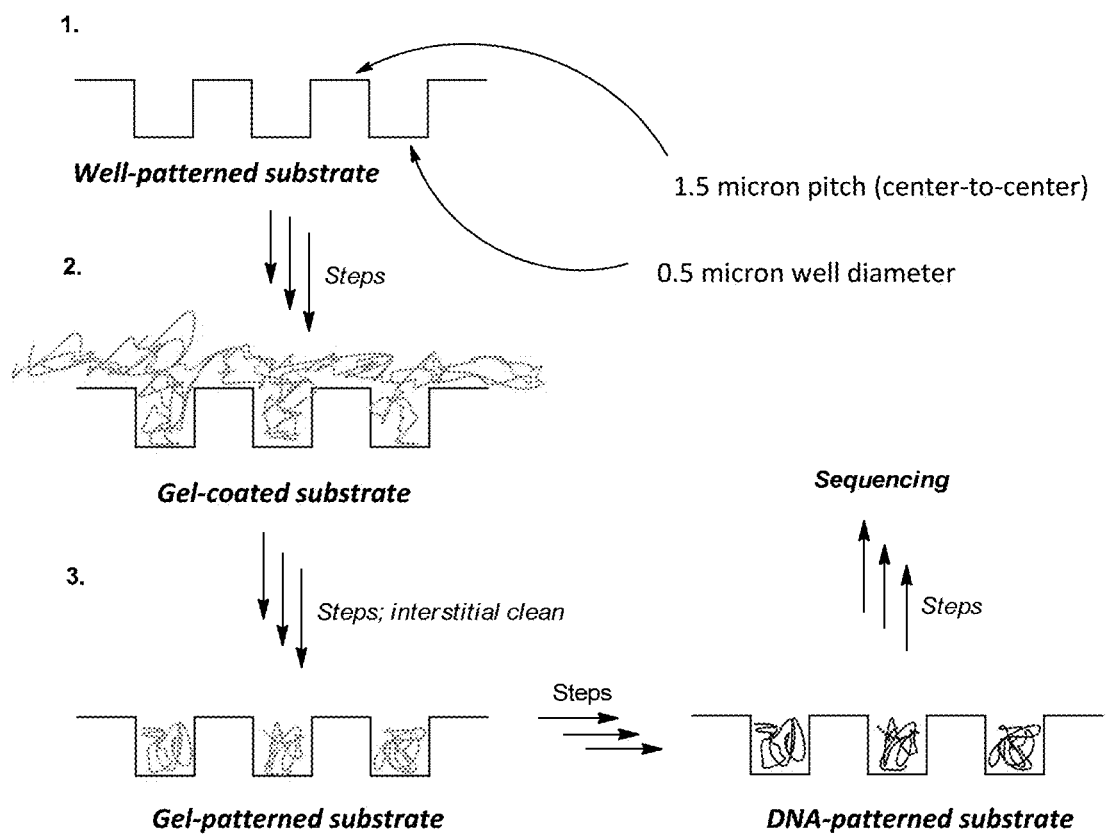
FIG. 1 shows a diagrammatic representation of a method for making and using a patterned array of DNA features, wherein each feature is a well having gel material that is attached to a cluster of DNA and the array is used in a sequencing technique.

An exemplary process for making a patterned array of nucleic acids is shown in FIG. 1. A profile view of a well-patterned substrate is shown diagrammatically. The wells have a pitch (center-to-center spacing) of 1.5 µm and the diameter of each well is 0.5 µm in the example. The well patterned substrate can be coated with a gel material such that material enters the wells and coats the interstitial regions. The resulting gel-coated substrate can be polished to remove gel material from the interstitial regions, leaving gel material in the wells, thereby forming a gel-patterned substrate. The gel can function to support capture of a DNA template and amplification of the template. For example, the gel can be grafted with oligonucleotide primers prior to surface coating, after surface coating and before polishing, or after polishing. The primers can function to capture the DNA templates and to prime amplification using the captured templates. The resulting DNA-patterned substrate can be analyzed for example in a sequencing technique.

A patterned array of nucleic acids in gel-containing wells provides multiple advantages for DNA sequencing. Examples of advantages compared to random arrays (i.e. arrays having a random pattern of features) include increased density of feature packing, increased control and tuning of feature density using concentration-independent template seeding, reduced processing requirements for image registration and increased ease of signal extraction. A further advantage can be derived from spatial confinement of nucleic acid populations provided by each feature. A feature of a patterned array of the present disclosure can function to restrict the area or volume within which a nucleic acid colony will grow (for example, via cluster amplification). Absent area or volume restrictions, some nucleic acid colonies may amplify to a larger size than others due to differences in percent content of guanine and cytosine in their sequences (i.e. GC content) which influence relative amplification rates. For the methods and compositions set forth herein, the volume or area of individual features can be selected to prevent or minimize differences in nucleic acid colony sizes that would otherwise occur from an amplification reaction due to differences in GC content between the template species being amplified. For example, the volume or area of the features can be sufficiently small to cap growth of the fastest growing colonies while allowing slower growing colonies to effectively fill the feature upon completion of the amplification reaction.

In particular embodiments, this disclosure provides fabrication of wells (e.g. microwells or nanowells) on glass, silicon, plastic or other suitable solid supports with patterned, covalently-linked gel such as poly(N-(5-azidoacetamidylpentyl)acrylamide-co-acrylamide) (PAZAM, see, for example, U.S. Prov. Pat. App. Ser. No. 61/753,833, which is incorporated herein by reference). The process creates gel pads used for sequencing that can be stable over sequencing runs with a large number of cycles. The covalent linking of the polymer to the wells is helpful for maintaining the gel in the structured features throughout the lifetime of the structured substrate during a variety of uses. However in many embodiments, the gel need not be covalently linked to the wells. For example, in some conditions silane free acrylamide (SFA, see, for example, US Pat. App. Pub. No. 2011/0059865 A1, which is incorporated herein by reference) which is not covalently attached to any part of the structured substrate, can be used as the gel material.

In particular embodiments, a structured substrate can be made by patterning a solid support material with wells (e.g. microwells or nanowells), coating the patterned support with a gel material (e.g. PAZAM, SFA or chemically modified variants thereof, such as the azidolyzed version of SFA (azido-SFA)) and polishing the gel coated support, for example via chemical or mechanical polishing, thereby retaining gel in the wells but removing or inactivating substantially all of the gel from the interstitial regions on the surface of the structured substrate between the wells. Primer nucleic acids can be attached to gel material. A solution of target nucleic acids (e.g. a fragmented human genome) can then be contacted with the polished substrate such that individual target nucleic acids will seed individual wells via interactions with primers attached to the gel material; however, the target nucleic acids will not occupy the interstitial regions due to absence or inactivity of the gel material. Amplification of the target nucleic acids will be confined to the wells since absence or inactivity of gel in the interstitial regions prevents outward migration of the growing nucleic acid colony. The process is conveniently manufacturable, being scalable and utilizing conventional micro- or nanofabrication methods.

In particular embodiments, fiducial markers are included on a structured substrate to facilitate identification and localization of individual features (e.g. wells or other gel-containing concave features). Fiducial markers are particularly useful for structured substrates having a spatially ordered pattern of features since the fiducial markers provide a point of reference for relative locations of other features. Fiducial markers can be used for registering images of random arrays as well, but the inherent disorder of clusters can be used instead, for example, as used with random arrays generated on commercial sequence platforms such as the HiSeq, Genome Analyzer or MiSeq platforms from Illumina, Inc. (San Diego, Calif.). Fiducial markers are especially beneficial for applications where the structured substrate is detected repeatedly to follow changes occurring at individual features over time. Fiducial markers allow individual nucleic acid clusters to be followed through sequential images obtained over multiple sequencing cycles, such that the sequence of individual clusters can be discretely determined.

This disclosure provides a fiducial marker having a pattern of concave region(s) and interstitial region(s). An exemplary design for a fiducial marker is a set of concentric circles having an alternating pattern of two or more of the following: a concave ring, interstitial ring and a ring of wells or other concave features (e.g. a "bulls-eye"). In some embodiments concave region(s) of a fiducial marker contain gel material, whereas interstitial regions do not. This differential location of the gel on the surface can be achieved using the gel coating and polishing methods set forth herein. Typically a detection method is used that can distinguish gel-containing regions from interstitial regions. In some cases, the distinction can be based on the presence of a particular analyte in the gel regions that is absent from the interstitial regions. For example, in the case of nucleic acid arrays, the gel-containing region of a fiducial marker can contain nucleic acids that are labeled via the same methods that are used to label target nucleic acids on the array. Thus, fiducial markers can be conveniently fabricated using the same methods used to fabricate analyte features. Accordingly, if desired, fiducial markers and analyte features can be fabricated simultaneously across one or more steps. Another useful fiducial marker that can be used in the structured substrates and methods set forth herein is one having sub-regions where the pattern of wells (or other concave features) in one subregion is rotated with respect to the pattern in another subregion. Such fiducial grids can be configured and used for image registration as set forth in U.S. Ser. No. 13/267,565, which is incorporated herein by reference.

As a further example, beads can be used as a fiducial. The beads can include a label such as a fluorophore. In this case, a surface can have at least two types of wells (or other concave features). Relatively large wells can accommodate one or more fiducial beads, whereas smaller wells, being too small to contain a bead, will only have gel material. Thus, the smaller wells function as analytical features for analysis and the larger, bead-filled wells function as fiducials. As an alternative to wells the fiducial features can be channels, such as those present in the bulls-eye configuration exemplified above, and the channels can have dimensions that accommodate the beads. As such, several beads can be placed in the channel to create a fiducial, for example, in the apparent shape of a string of beads.

Patterned arrays, methods for their manufacture and methods for their use are exemplified herein with regard to a gel material that is used to attach analytes of interest. It will be understood that the gel material is exemplary and can be replaced with other organic materials that can be used to mediate localization of analytes to features on a surface. Such organic materials include for example, polymers that may form a surface coating and may not necessarily be considered as gels, per se. A specific example is a polymer formed by ATRP (atom transfer radical polymerization) or surface initiated polymerization processes. Methods set forth herein for applying gel material to a surface, removing the gel material from interstitial regions, using the resulting arrays in analytical or preparative methods etc., can be readily adapted for use with non-gel materials.

Terms used herein will be understood to take on their ordinary meaning in the relevant art unless specified otherwise. Several terms used herein and their meanings are set forth below.

As used herein, the term "attached" refers to the state of two things being joined, fastened, adhered, connected or bound to each other. For example, an analyte, such as a nucleic acid, can be attached to a material, such as a gel or solid support, by a covalent or non-covalent bond. A covalent bond is characterized by the sharing of pairs of electrons between atoms. A non-covalent bond is a chemical bond that does not involve the sharing of pairs of electrons and can include, for example, hydrogen bonds, ionic bonds, van der Waals forces, hydrophilic interactions and hydrophobic interactions.

As used herein, the term "clonal population" refers to a population of nucleic acids that is homogeneous with respect to a particular nucleotide sequence. The homogenous sequence is typically at least 10 nucleotides long, but can be even longer including for example, at least 50, 100, 250, 500, 1000 or 2500 nucleotides long. A clonal population can be derived from a single target nucleic acid or template nucleic acid. A clonal population can include at least 2, 5, 10, 100, 1000 or more copies of a target nucleotide sequence. The copies can be present in a single nucleic acid molecule, for example, as a concatamer or the copies can be present on separate nucleic acid molecules (i.e. a clonal population can include at least 2, 5, 10, 100, 1000 or more nucleic acid molecules having the same target nucleotide sequence). Typically, all of the nucleic acids in a clonal population will have the same nucleotide sequence. It will be understood that a negligible number of contaminant nucleic acids or mutations (e.g. due to amplification artifacts) can occur in a clonal population without departing from clonality. Thus, a population can be at least 80%, 90%, 95% or 99% clonal. In some cases 100% pure clonal populations may be present.

As used herein, the term "coat," when used as a verb, is intended to mean providing a layer or covering on a surface. At least a portion of the surface can be provided with a layer or cover. In some cases the entire surface can be provided with a layer or cover. In alternative cases only a portion of the surface will be provided with a layer or covering. The term "coat," when used to describe the relationship between a surface and a material, is intended to mean that the material is present as a layer or cover on the surface. The material can seal the surface, for example, preventing contact of liquid or gas with the surface. However, the material need not form a seal. For example, the material can be porous to liquid, gas, or one or more components carried in a liquid or gas. Exemplary materials that can coat a surface include, but are not limited to, a gel, polymer, organic polymer, liquid, metal, a second surface, plastic, silica, or gas.

As used herein, the term "concave feature," when used in reference to a solid support, refers to a recess or indentation in the solid support. Exemplary concave features include, but are not limited to, a well, pit, hole, depression, channel, or trough. A concave feature can optionally have a curved cross section (in the dimension orthogonal to the surface of the solid support); however, a cross section with one or more linear sections, angles or corners is also possible. Cross sections with combinations of curved and linear sections are also possible. Generally, a concave feature need not pass completely through the solid support, for example, instead having a bottom surface or point in the substrate.

As used herein, the term "different", when used in reference to nucleic acids, means that the nucleic acids have nucleotide sequences that are not the same as each other. Two or more nucleic acids can have nucleotide sequences that are different along their entire length. Alternatively, two or more nucleic acids can have nucleotide sequences that are different along a substantial portion of their length. For example, two or more nucleic acids can have target nucleotide sequence portions that are different for the two or more molecules while also having a universal sequence portion that is the same on the two or more molecules.

As used herein, the term "each," when used in reference to a collection of items, is intended to identify an individual item in the collection but does not necessarily refer to every item in the collection. Exceptions can occur if explicit disclosure or context clearly dictates otherwise.

As used herein, the term "fluidic access," when used in reference to a molecule in a fluid and a site in contact with the fluid, refers to the ability of the molecule to move in or through the fluid to contact or enter the site. The term can also refer to the ability of the molecule to separate from or exit the site to enter the solution. Fluidic access can occur when there are no barriers that prevent the molecule from entering the site, contacting the site, separating from the site and/or exiting the site. However, fluidic access is understood to exist even if diffusion is retarded, reduced or altered so long as access is not absolutely prevented.

As used herein, the term "gel material" is intended to mean a semi-rigid material that is permeable to liquids and gases. Typically, gel material can swell when liquid is taken up and can contract when liquid is removed by drying. Exemplary gels include, but are not limited to those having a colloidal structure, such as agarose; polymer mesh structure, such as gelatin; or cross-linked polymer structure, such as polyacrylamide, SFA (see, for example, US Pat. App. Pub. No. 2011/0059865 A1, which is incorporated herein by reference) or PAZAM (see, for example, U.S. Prov. Pat. App. Ser. No. 61/753,833, which is incorporated herein by reference). Particularly useful gel material will conform to the shape of a well or other concave feature where it resides. Some useful gel materials can both (a) conform to the shape of the well or other concave feature where it resides and (b) have a volume that does not substantially exceed the volume of the well or concave feature where it resides.

As used herein, the term "interstitial region" refers to an area in a substrate or on a surface that separates other areas of the substrate or surface. For example, an interstitial region can separate one concave feature of an array from another concave feature of the array. The two regions that are separated from each other can be discrete, lacking contact with each other. In another example, an interstitial region can separate a first portion of a feature from a second portion of a feature. In many embodiments the interstitial region is continuous whereas the features are discrete, for example, as is the case for an array of wells in an otherwise continuous surface. The separation provided by an interstitial region can be partial or full separation. Interstitial regions will typically have a surface material that differs from the surface material of the features on the surface. For example, features of an array can have an amount or concentration of gel material or analytes that exceeds the amount or concentration present at the interstitial regions. In some embodiments the gel material or analytes may not be present at the interstitial regions.

As used herein, the term "library," when used in reference to analytes, refers to a collection of analytes having different chemical compositions. Typically, the analytes in a library will be different species having a common feature or characteristic of a genera or class, but otherwise differing in some way. For example, a library can include nucleic acid species that differ in nucleotide sequence, but that are similar with respect to having a sugar-phosphate backbone.

As used herein, the terms "nucleic acid" and "nucleotide" are intended to be consistent with their use in the art and to include naturally occurring species or functional analogs thereof. Particularly useful functional analogs of nucleic acids are capable of hybridizing to a nucleic acid in a sequence specific fashion or capable of being used as a template for replication of a particular nucleotide sequence. Naturally occurring nucleic acids generally have a backbone containing phosphodiester bonds. An analog structure can have an alternate backbone linkage including any of a variety of those known in the art. Naturally occurring nucleic acids generally have a deoxyribose sugar (e.g. found in deoxyribonucleic acid (DNA)) or a ribose sugar (e.g. found in ribonucleic acid (RNA)). A nucleic acid can contain nucleotides having any of a variety of analogs of these sugar moieties that are known in the art. A nucleic acid can include native or non-native nucleotides. In this regard, a native deoxyribonucleic acid can have one or more bases selected from the group consisting of adenine, thymine, cytosine or guanine and a ribonucleic acid can have one or more bases selected from the group consisting of uracil, adenine, cytosine or guanine. Useful non-native bases that can be included in a nucleic acid or nucleotide are known in the art. The terms "probe" or "target," when used in reference to a nucleic acid, are intended as semantic identifiers for the nucleic acid in the context of a method or composition set forth herein and does not necessarily limit the structure or function of the nucleic acid beyond what is otherwise explicitly indicated. The terms "probe" and "target" can be similarly applied to other analytes such as proteins, small molecules, cells or the like.

As used herein, the term "random pattern," when used in reference to wells on a surface, means that the relative locations of a subset of wells in one region of the surface is not known or predictable from the locations of a subset of wells in another region of the surface. The subset used for the measure will generally include at least 3 wells but can include at least, 4, 5, 6, 10 or more wells. A random pattern generally does not include multiple repetitions of any sub-patterns. The term can be applied to other concave features besides wells.

As used herein, the term "repeating pattern," when used in reference to wells on a surface, means that the relative locations of a subset of wells in one region of the surface is the same as the relative locations of a subset of wells in at least one other region of the surface. Thus, the relative locations for wells in one region of a repeating pattern are generally predictable from the relative locations of wells in another region of the repeating pattern. The subset used for the measure will generally include at least 3 wells but can include at least, 4, 5, 6, 10 or more wells. Exemplary repeating patterns include rectilinear patterns and hexagonal patterns. A repeating pattern can include multiple repetitions of a sub-pattern. The term can be applied to other concave features besides wells.

As used herein, the term "segregate," when used in reference to gel material in two wells (or at two other features), means to separate or isolate the gel material in one of the wells (or at one of the features) from the gel material in the other well (or at the other feature). Thus, the gel material in the first well (or at the first feature) is not in direct contact with the gel material in the other well (or at the other feature). In some embodiments, the gel material in the two wells (or at the two features) is in indirect contact, for example, via a solution that contacts the two wells (or features). Alternatively, the gel material in the two wells (or at the two features) is not even in indirect contact. An interstitial region on a surface can segregate the gel material in two wells (or at two features) by being devoid of the gel material. In particular embodiments, a gel material can be discontinuous on a surface, being present at concave features, such as wells, but not present at interstitial regions between the features.

As used herein, the term "surface" is intended to mean an external part or external layer of a solid support or gel material. The surface can be in contact with another material such as a gas, liquid, gel, polymer, organic polymer, second surface of a similar or different material, metal, or coat. The surface, or regions thereof, can be substantially flat. The surface can have surface features such as wells, pits, channels, ridges, raised regions, pegs, posts or the like.

As used herein, the term "single species" means substantially one and only one species of a particular genera. The term is not necessarily intended to limit the number of representatives of a single species that are present. For example, a population of nucleic acid molecules each having the same nucleotide sequence comprise a single species of nucleic acid. The term "single" in this context is not intended to exclude the presence of other things that are not within the relevant genera. For example, a well that contains a single species of target nucleic acid from a library can include multiple nucleic acids having the same sequence, will exclude other target nucleic from the library, but need not necessarily exclude any other non-nucleic acid components. It will be understood that an apparent single species population can have a small amount of another species present at a level that is considered by those skilled in the art to be a negligible level of contamination or artifact for the particular use of the population. For example, a nucleic acid cluster, derived from a single template having a first sequence, will be considered to have an apparent single species if the amount of any nucleic acid molecules having a second sequence is sufficiently low to be undetectable or ignored when the first sequence is detected. Alternatively, an absolute single species population will have one and only one species.

As used herein, the term "solid support" refers to a rigid substrate that is insoluble in aqueous liquid. The substrate can be non-porous or porous. The substrate can optionally be capable of taking up a liquid (e.g. due to porosity) but will typically be sufficiently rigid that the substrate does not swell substantially when taking up the liquid and does not contract substantially when the liquid is removed by drying. A nonporous solid support is generally impermeable to liquids or gases. Solid supports can optionally be inert to a chemistry that is used to modify a gel. For example, a solid support can be inert to chemistry used to attach analytes, such as nucleic acids, to gels in a method set forth herein. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, metals, inorganic glasses, optical fiber bundles, and polymers. Particularly useful solid supports for some embodiments are located within a flow cell apparatus. Exemplary flow cells are set forth in further detail below.

As used herein, the term "well" refers to a discrete concave feature in a solid support having a surface opening that is completely surrounded by interstitial region(s) of the surface. Wells can have any of a variety of shapes at their opening in a surface including but not limited to round, elliptical, square, polygonal, star shaped (with any number of vertices) etc. The cross section of a well taken orthogonally with the surface can be curved, square, polygonal, hyperbolic, conical, angular, etc.

The embodiments set forth below and recited in the claims can be understood in view of the above definitions.

The present disclosure provides a substrate that includes a solid support having a surface, the surface having at least one concave feature, the at least one concave feature containing a gel material, the at least one concave feature being bordered by at least one interstitial region on the surface; and a library of analytes in the gel material, wherein the gel material in each of the wells includes a single species of the analytes of the library.

In some embodiments the substrate is configured as an array of wells and the analytes are nucleic acids. Accordingly, this disclosure provides an array that includes a solid support having a surface, the surface having a plurality of wells, the wells containing a gel material, the wells being separated from each other by interstitial regions on the surface, the interstitial regions segregating the gel material in each of the wells from the gel material in other wells of the plurality; and a library of target nucleic acids in the gel material, wherein the gel material in each of the wells includes a single species of the target nucleic acids of the library.

A solid support used in a structured substrate set forth herein can be made from any of a variety of materials set forth herein, for example, above in the definitions, below in the examples or immediately following. A particularly useful material is glass. Other suitable substrate materials may include polymeric materials, plastics, silicon, quartz (fused silica), borofloat glass, silica, silica-based materials, carbon, metals, an optical fiber or optical fiber bundles, sapphire, or plastic materials such as COCs and epoxies. The particular material can be selected based on properties desired for a particular use. For example, materials that are transparent to a desired wavelength of radiation are useful for analytical techniques that will utilize radiation of the desired wavelength, such as one or more of the techniques set forth herein. Conversely, it may be desirable to select a material that does not pass radiation of a certain wavelength (e.g. being opaque, absorptive or reflective). This can be useful for formation of a mask to be used during manufacture of the structured substrate, such as a method set forth herein; or to be used for a chemical reaction or analytical detection carried out using the structured substrate, such as those set forth herein. Other properties of a material that can be exploited are inertness or reactivity to certain reagents used in a downstream process, such as those set forth herein; or ease of manipulation or low cost during a manufacturing process manufacture, such as those set forth herein. Further examples of materials that can be used in the structured substrates or methods of the present disclosure are described in U.S. Ser. No. 13/661,524 and US Pat. App. Pub. No. 2012/0316086 A1, each of which is incorporated herein by reference.

In a particular embodiment, a Sol-Gel based substrate can be made and used. Sol-Gel based patterning can be accomplished by coating a rigid or flexible substrate, such as glass, silicon, plastic, metal or the like, with a Sol-Gel coating can be carried out, for example, through spin coating, dipping or spray coating. The Sol-Gel can be provided in a liquid state when applied to the substrate and can contain either photo- or thermal-initiators that enable curing (making the liquid a gel) through the exposure of the Sol-Gel to either light or heat. Subsequent to coating the substrate with the Sol-Gel, and prior to curing the material, the Sol-Gel can be imprinted with a template (three dimensional stamp) that has either a single or plurality of protruding feature(s). The template can be made, for example, of silicon, glass (such as quartz), metal (such as nickel), plastic or polymer (such as PDMS). Imprinting of the stamp into the Sol-Gel can be accomplished by placing the template in contact with the Sol-Gel. When the template is in contact with the Sol-Gel, the Sol-Gel redistributes to conformally surround the structure of the template. When the template is in contact with the Sol-Gel, the redistribution of the Sol-Gel can be driven either through an external force applied to the template or the substrate, or through capillary forces intrinsic to the nature of the patterned template. When the template is in contact with the Sol-Gel, the stack of substrate+Sol-Gel+template can be exposed to light or heat to cure the Sol-Gel and to lock the pattern originally in the template into the Sol-Gel. This patterning process is conventionally referred to as nanoimprint lithography. Following curing of the Sol-Gel, the template can be separated from the substrate+Sol-Gel stack, and the template can be either discarded or re-used to pattern another substrate coated with un-cured Sol-Gel. The substrate with the cured, patterned Sol-Gel can then be taken into a chemical deposition process, or if a pure glass like surface is desired, the substrate+patterned Sol-Gel stack can be taken through a thermal process (sintering) that will remove organic material that was originally present in the Sol-Gel. This is not required but can make the substrate a pure $SiO_2$ material that has advantages in certain chemical attachment schemes.

Another approach to producing a patterned substrate is to use a plastic material such as COC or COP (such as Zeonor or Topas) and perform a thermal embossing process to create the array of indentations. The process is similar to nanoimprint lithography. A substrate of plastic can be mounted on a chuck that has the ability to be temperature controlled. The plastic substrate can then be heated to a temperature such that the outer skin of the plastic exceeds the glass transition temperature. While the substrate is at the elevated temperature, the template is put into hard contact with a template (e.g. quartz, silicon, polymeric or metallic). The template typically has an external force applied to ensure that the plastic completely conformally coats the structured template. While in contact at the elevated temperature, the plastic redistributes itself to become a negative replica of the template; for example if the template has an array of posts then the embossed plastic results in an array of wells. While the template is in contact with the plastic substrate, the temperature of the substrate is reduced thus locking the embossed pattern into the substrate.

A concave feature that is on a substrate can have any of a variety of shapes. In terms of the shape on the surface, the feature can have curved sides, linear sides, corners or a combination thereof. For example, the features can be wells having openings in the surface that are circular, oval, square, polygonal, star-shaped (with any number of vertices), or irregularly shaped. The features can be channels and the shape of the channels on the surface can include sides that are curved, linear, angled or a combination thereof. Other channel features can be linear, serpentine, rectangular, square, triangular, circular, oval, hyperbolic, or a combination thereof. The channels can have one or more branches or corners. The channels can connect two points on a surface, one or both of which can be the edge of the substrate. FIG.

Figure 3B:
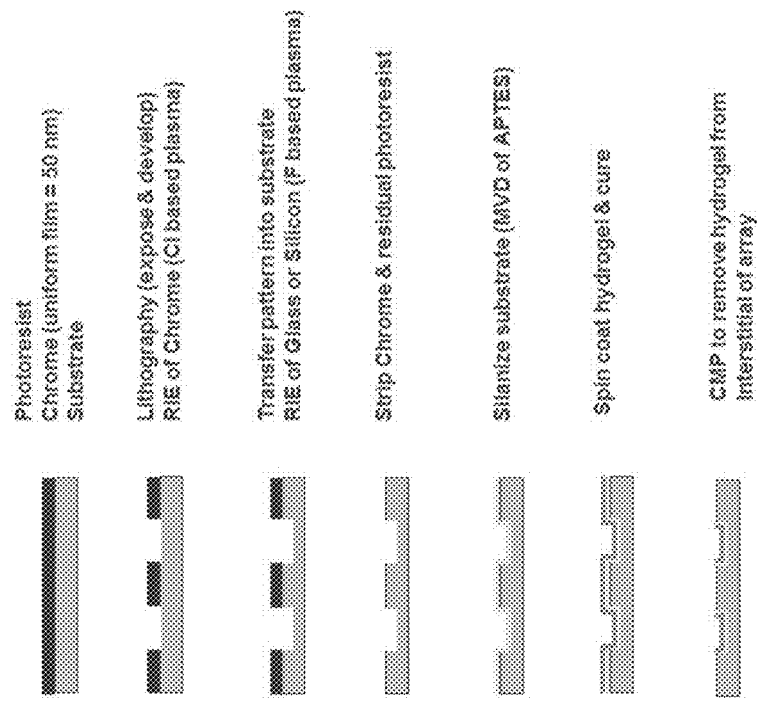
FIG. 3B shows example SEM images of wells and portions of a fiducial in a glass substrate.
Figure 3A:
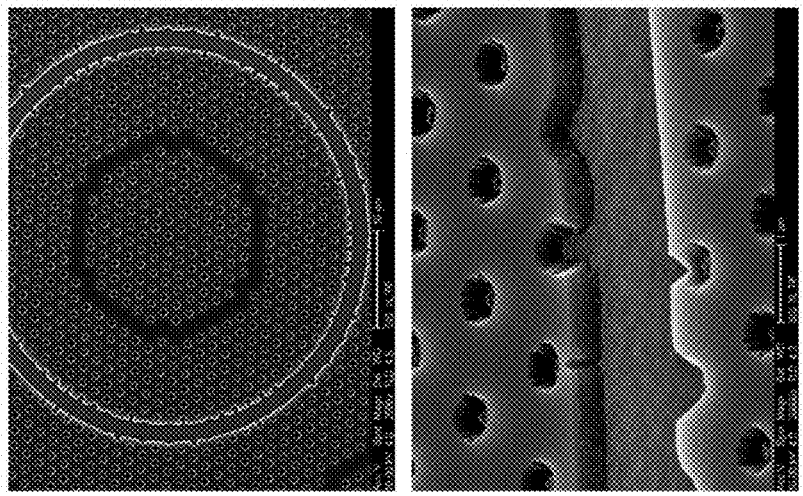
FIG. 3A shows a schematic process flow utilizing photolithography and a Cr hard mask along with reactive ion etching to fabricate concave features in a substrate.
Figure 3C:
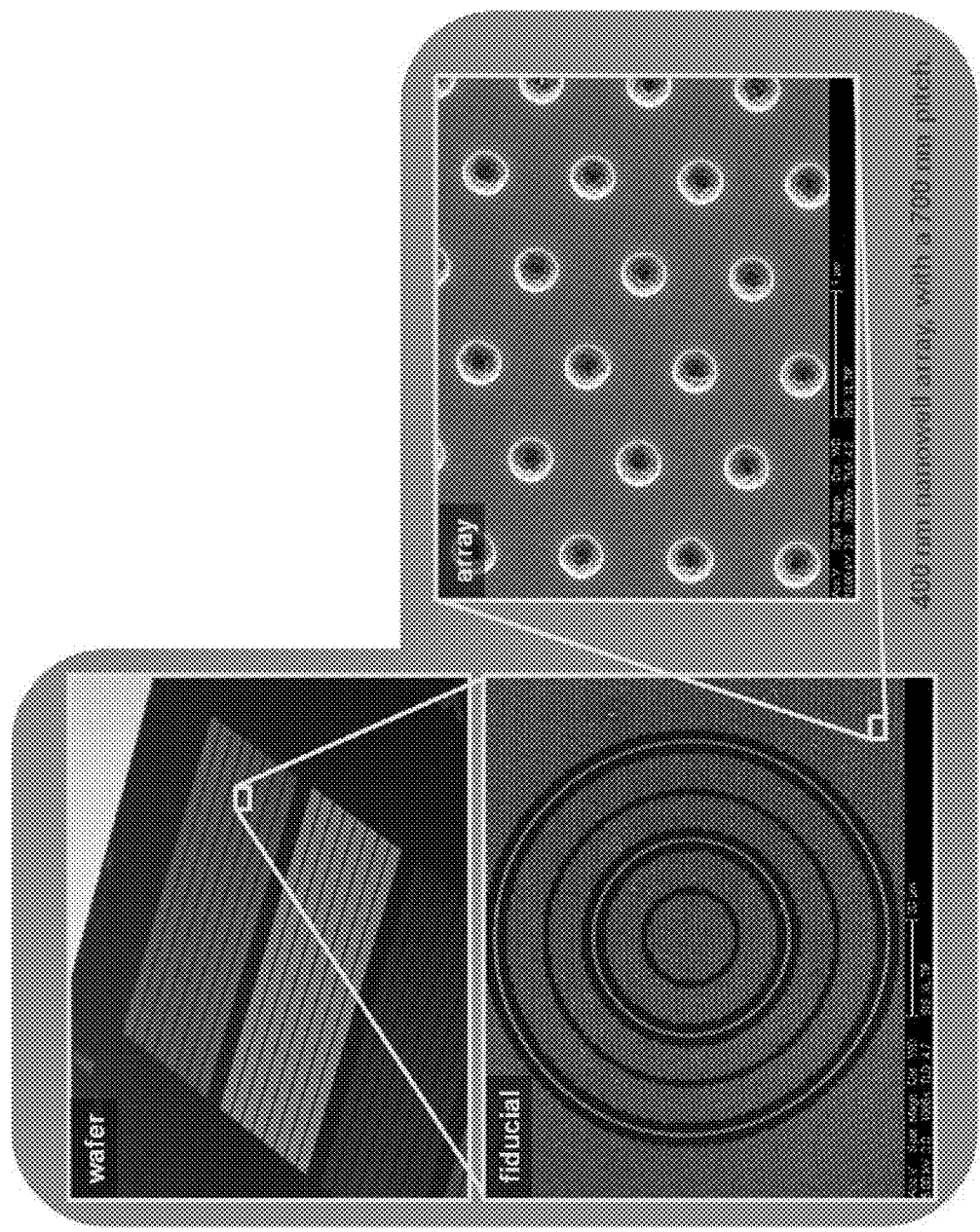
FIG. 3C shows an image of a wafer, an image of a portion of the wafer that includes a fiducial and an array of wells, and an image from a portion of the array that includes wells.

3B and FIG. 3C shows exemplary channel features in bulls-eye fiducials along with wells within and surrounding the bulls-eye fiducials.

The cross sectional shape of a concave feature, taken orthogonal to the surface, can have walls that are curved, linear or a combination of the two. Thus, the cross-sectional shape can be a portion of a circle or oval (e.g. U-shaped), or can have two or more linear sides that meet at corners (e.g. V-, square-, polygonal- or star-shaped). In terms of cross-sectional shape, the bottom of the concave feature can be narrower, wider, or roughly the same as the opening on the surface. These cross sectional shapes can be illustrated for the case where the concave feature is a well, in which case, the opening in the surface will be roughly the same area as the bottom of the well when the well has a cylindrical cross section, whereas the bottom of the well will have a different area (typically smaller) than the area at the opening on the surface when the well has a conical cross section. Of course, the cross sections, although illustrated for wells, can apply to channels also.

For embodiments where the concave features form wells, each well can have any volume that is capable of confining a liquid. The minimum or maximum volume can be selected, for example, to accommodate the throughput (e.g. multi-plexity), resolution, analyte composition, or analyte reactivity expected for downstream uses of the substrate. For example, the volume can be at least $1\times10^{-3}$ $\mu m^3$, $1\times10^{-2}$ $\mu m^3$, 0.1 $\mu m^3$, 1 $\mu m^3$, 10 $\mu m^3$, 100 $\mu m^3$ or more. Alternatively or additionally, the volume can be at most $1\times10^4$ $\mu m^3$, $1\times10^3$ $\mu m^3$, 100 $\mu m^3$, 10 $\mu m^3$, 1 $\mu m^3$, 0.1 $\mu m^3$ or less. It will be understood that gel material can fill all or part of the volume of a well. The volume of gel in an individual well can be greater than, less than or between the values specified above.

The area occupied by each well opening on a surface can be selected based upon similar criteria as those set forth above for well volume. For example, the area for each well opening on a surface can be at least $1\times10^{-3}$ $\mu m^2$, $1\times10^{-2}$ $\mu m^2$, 0.1 $\mu m^2$, 1 $\mu m^2$, 10 $\mu m^2$, 100 $\mu m^2$ or more. Alternatively or additionally, the area can be at most $1\times10^3$ $\mu m^2$, 100 $\mu m^2$, 10 $\mu m^2$, 1 $\mu m^2$, 0.1 $\mu m^2$, $1\times10^{-2}$ $\mu m^2$, or less. The depth of each well can be at least 0.1 μm, 1 μm, 10 μm, 100 μm or more. Alternatively or additionally, the depth can be at most $1\times10^3$ μm, 100 μm, 10 μm, 1 μm, 0.1 μm or less.

Many different layouts of wells or other concave features may be envisaged, including regular, repeating, and non-regular patterns. For example, wells can be disposed in a hexagonal grid for close packing and improved density. Other layouts may include, for example, rectilinear (i.e., rectangular) layouts, triangular layouts, and so forth. The particular layouts, and differences between the layouts of different domains, if used, may follow the teachings of U.S. Pat. No. 7,813,013, and/or of U.S. patent application Ser. No. 13/267,565, each of which is hereby incorporated by reference. Any of a variety of crystalline or poly-crystalline patterns can be useful.

A pattern of wells can be characterized in terms of the average pitch (i.e. center-to-center spacing) for the wells. Again, the pattern can be regular such that the coefficient of variation around the average pitch is small or the pattern can be non-regular in which case the coefficient of variation can be relatively large. In either case, the average pitch can be, for example, at least 10 nm, 0.1 μm, 0.5 μm, 1 μm, 5 μm, 10 μm, 100 μm or more. Alternatively or additionally, the average pitch can be, for example, at most 100 μm, 10 μm, 5 μm, 1 μm, 0.5 μm 0.1 μm or less. Of course, the average pitch for a particular pattern of wells can be between one of the lower values and one of the upper values selected from the ranges above.

A pattern of wells can also be characterized with respect to the density of wells (i.e. number of wells) in a defined area. For example, the wells may be present at a density of approximately 2 million per $mm^2$. In accordance with the manufacturing methods set forth herein, the density can easily be tuned to different densities including, for example, a density of at least 100 per $mm^2$, 1,000 per $mm^2$, 0.1 million per $mm^2$, 1 million per $mm^2$, 2 million per $mm^2$, 5 million per $mm^2$, 10 million per $mm^2$, 50 million per $mm^2$ or more. Alternatively or additionally, the density can be tuned to be no more than 50 million per $mm^2$, 10 million per $mm^2$, 5 million per $mm^2$, 2 million per $mm^2$, 1 million per $mm^2$, 0.1 million per $mm^2$, 1,000 per $mm^2$, 100 per $mm^2$ or less. Of course, the density of wells on a substrate can be between one of the lower values and one of the upper values selected from the ranges above.

In particular embodiments, a gel material is used. In some cases, a gel-forming (e.g. polymerizable) material is provided to a solid support in a liquid state and subsequently converted to a gel. Examples of polymerizable materials include, without limitation, acrylamide, methacrylamide, hydroxyethyl methacrylate, N-vinyl pyrolidinone or derivatives thereof. Such materials are useful for preparing hydrogels. In some embodiments, the polymerizable material can include two or more different species of compound that form a co-polymer. For example, two or more different species of acrylamide, methacrylamide, hydroxyethyl methacrylate, N-vinyl pyrolidinone or derivatives thereof can function as co-monomers that polymerize to form a copolymer hydrogel. Useful hydrogels include, but are not limited to, silane-free acrylamide (SFA) polymer (see US Pat. App. Pub. No. 2011/0059865 A1, which is incorporated herein by reference), poly(N-(5-azidoacetamidylpentyl)acrylamide-co-acrylamide) (PAZAM, see U.S. Prov. Pat. App. Ser. No. 61/753,833, which is incorporated herein by reference), polyacrylamide polymers formed from acrylamide and an acrylic acid or an acrylic acid containing a vinyl group as described, for example, in WO 00/31148 (incorporated herein by reference); polyacrylamide polymers formed from monomers that form [2+2] photo-cycloaddition reactions, for example, as described in WO 01/01143 or WO 03/014392 (each of which is incorporated herein by reference); or polyacrylamide copolymers described in U.S. Pat. No. 6,465,178, WO 01/62982 or WO 00/53812 (each of which is incorporated herein by reference). Chemically treated variants of these gel materials are also useful, such as chemically treated SFA made to react with oligonucleotides having a corresponding reactive group (such as the azidolysis of SFA to produce azido-SFA which is reactive with a 5'- or 3'-alkynyl modified oligonucleotides) Exemplary hydrogels and polymerizable materials that can be used to form hydrogels are described, for example, in U.S. Ser. No. 61/753,833 or US Pat. App. Pub. No. 2011/0059865 A1, each of which is incorporated herein by reference. Other useful gels are those that are formed by a temperature dependent change in state from liquid to gelatinous. Examples include, but are not limited to agar, agarose, or gelatin.

The gel material that is in a well or other concave feature on the surface of a structured substrate can be covalently attached to the surface. For example, PAZAM can be covalently attached to a surface using surface materials and other reagents set forth in U.S. Ser. No. 61/753,833, which is incorporated herein by reference, and as set forth in the Examples section herein. However, the gel material need not be covalently attached to wells or other concave features as exemplified for SFA in the Examples section below.

One or more analytes can be present in or on the gel material that is present on a structured substrate. The gel-containing substrates of the present disclosure are particularly useful for detection of analytes, or for carrying out synthetic reactions with analytes. Thus, any of a variety of analytes that are to be detected, characterized, modified, synthesized, or the like can be present in or on gel material of a substrate set forth herein. Exemplary analytes include, but are not limited to, nucleic acids (e.g. DNA, RNA or analogs thereof), proteins, polysaccharides, cells, antibodies, epitopes, receptors, ligands, enzymes (e g kinases, phosphatases or polymerases), small molecule drug candidates, or the like. A structured substrate can include multiple different species from a library of analytes. For example, the species can be different antibodies from an antibody library, nucleic acids having different sequences from a library of nucleic acids, proteins having different structure and/or function from a library of proteins, drug candidates from a combinatorial library of small molecules etc.

In some embodiments, analytes can be distributed on a structured substrate such that they are individually resolvable. For example, a single molecule of each analyte can be present in each gel-containing well of a structured substrate. Alternatively, analytes can be present as colonies or populations such that individual molecules are not necessarily resolved. The colonies or populations can be homogenous with respect to containing only a single species of analyte (albeit in multiple copies). Taking nucleic acids as an example, each well on a structured substrate can include a colony or population of nucleic acids and every nucleic acid in the colony or population can have the same nucleotide sequence (either single stranded or double stranded). Such colonies can be created by cluster amplification or bridge amplification as set forth in further detail elsewhere herein. Multiple repeats of a target sequence can be present in a single nucleic acid molecule, such as a concatamer created using a rolling circle amplification procedure. Thus, the gel material in each well on a structured substrate can contain multiple copies of a single species of an analyte. Alternatively, a colony or population of analytes that are in a well can include two or more different species. For example, one or more wells on a structured substrate can each contain a mixed colony having two or more different nucleic acid species (i.e. nucleic acid molecules with different sequences). The two or more nucleic acid species in a mixed colony can be present in non-negligible amounts, for example, allowing more than one nucleic acid to be detected in the mixed colony.

Analytes can be attached to a gel material. The attachment can be covalent or non-covalent. Exemplary methods and reactants for attaching nucleic acids to gels are described, for example, in US Pat. App. Pub. No. 2011/0059865 A1, or U.S. Prov. Pat. App. Ser. No. 61/753,833, each of which is incorporated herein by reference. The analytes can be nucleic acids and the nucleic acids can be attached to the gel via their 3' oxygen, 5' oxygen, or at other locations along their length such as via a base moiety of the 3' terminal nucleotide, a base moiety of the 5' nucleotide, and/or one or more base moieties elsewhere in the molecule. Non-covalent modes of attachment include, for example, ionic interactions between nucleic acid and gel, entrapment of nucleic acid within pores of a gel, protein-protein interactions, binding between receptors and ligands on the gel and/or nucleic acid, and other known modes.

In some embodiments a gel coating that is applied to a surface contains one or more analytes prior to removal of gel material from the interstitial regions. Thus, gel material can be present at the interstitial regions and the gel material at the interstitial regions can be attached to one or more different analytes. Alternatively, analytes are added to a gel material in concave features after removing gel material from the interstitial regions.

A structured substrate of the present disclosure can occur in a flow cell. Exemplary flow cells, methods for their manufacture and methods for their use are described in US Pat. App. Publ. Nos. 2010/0111768 A1 or 2012-0270305 A1; or WO 05/065814, each of which is incorporated herein by reference. Flow cells provide a convenient format for housing an array that is produced by the methods of the present disclosure and that is subjected to a sequencing-by-synthesis (SBS) or other technique that involves repeated delivery of reagents in cycles (e.g. synthesis techniques or detection techniques having repetitive or cyclic steps). Exemplary detection methods are set forth in further detail below.

In some embodiments a flow-cell or other vessel having multiple surfaces is used. Vessels having multiple surfaces can be used such that only a single surface has gel-containing concave features (e.g. wells). Alternatively two or more surfaces present in the vessel can have gel-containing concave features. One or more surfaces of a flow cell can be selectively detected. For example, opposing surfaces in the interior of a flow cell can be selectively addressed with focused radiation using methods known in the art such as confocal techniques. Useful confocal techniques and devices for selectively directing radiation to multiple surfaces of a vessel (e.g. a flow cell) are described, for example, in US Pat. App. Pub. No. 2009/0272914 A1 or U.S. Pat. No. 8,039,817, each of which is incorporated herein by reference.

The present disclosure provides a method of making a substrate. The method can include the steps of (a) providing a solid support having a planar surface, wherein the planar surface is interrupted by one or more concave features and wherein the one or more concave features are bordered by one or more interstitial regions on the planar surface; (b) coating at least a portion of the solid support with a gel material, wherein the portion includes at least one of the concave features and at least one of the interstitial regions; and (c) polishing the planar surface to remove the gel material from the at least one interstitial regions and to maintain the gel material in the at least one concave feature.

A substrate can be fabricated to have concave features using any of a variety of techniques known in the art. In many embodiments, the concave features will be small, on the order of nanometer or micrometer dimensions. In such cases nanofabrication or microfabrication techniques can be used. Examples of these techniques are set forth elsewhere herein such as in Example II below. Further exemplary nanofabrication and microfabrication techniques are described in U.S. Ser. No. 13/661,524 and US Pat. App. Publ. No. 2012/0316086 A1, each of which is incorporated herein by reference.

One or more concave features, such as wells, can be coated with preformed gel material or with a liquid that subsequently forms a gel material. An example of the former approach is the coating of a substrate with preformed PAZAM using spin coating, dipping, flow of the gel under positive or negative pressure or techniques set forth in U.S. Prov. Pat. App. Ser. No. 61/753,833, which is incorporated herein by reference. Coating of an array of wells with preformed PAZAM is demonstrated below in Example III.

An example of applying liquid that subsequently forms a gel material is the coating of an array of wells with silane free acrylamide and N-[5-(2-bromoacetyl) aminopentyl]acrylamide (BRAPA) in liquid form and allowing the reagents to form a gel by polymerization on the surface. Coating of an array in this way is demonstrated in Example I below and can use chemical reagents and procedures as set forth in US Pat. App. Pub. No. 2011/0059865 A1, which is incorporated herein by reference. In some embodiments, for example, when a well-containing substrate is dipped into a preformed gel material, the gel material may fill the wells selectively and polishing may not be necessary.

Analytes can be added to a gel material prior to contact with a solid support or afterward. Furthermore, analytes can be added to a gel (i.e. after the gel has formed from its precursor reagents) or analytes can be added to a gel forming reagent solution (i.e. prior to gel formation). In some embodiments various analytes can be added prior to gel formation and others can be added after gel formation. In one example, primer nucleic acids are added to a gel forming solution and the solution is then allowed to form into a gel (e.g. by polymerization as occurs for SFA and PAZAM). The gel formation may occur on a solid support or the gel may be preformed and then coated onto a solid support. Either way, the primers will be attached to the gel that is present in concave features such as wells. Target nucleic acids that are complementary to the primers can then be added to the primer-containing gel such that the target nucleic acids become attached to the gel (via hybridization) after the gel material has been coated onto the solid support. The hybridization of the target nucleic acids can optionally occur after a polishing step has been carried out (polishing is described in further detail below). The preceding example, describes several instances where nucleic acids (either functioning as primers or targets) are added to a gel at different stages of the manufacture of a structured substrate.

In several embodiments, primer nucleic acids that are attached to a gel (or otherwise present in or on a gel) can be used for capture and/or amplification of template nucleic acids. The primers can be universal primers that hybridize to a universal adapter sequence that is attached to different target nucleic acids in a library (i.e. each target nucleic acid includes a target region that differs from other target nucleic acids in the library and several target nucleic acids in the library have the same universal adapter sequence). In some embodiments, a target nucleic acid can be attached to gel material, and primers (whether in solution or also attached to the gel) can be used to amplify the attached target nucleic acid (i.e. the target nucleic acid can serve as a template for amplification).

A method set forth herein can use any of a variety of amplification techniques. Exemplary techniques that can be used include, but are not limited to, polymerase chain reaction (PCR), rolling circle amplification (RCA), multiple displacement amplification (MDA), or random prime amplification (RPA). In particular embodiments, one or more primers used for amplification can be attached to a gel material. In PCR embodiments, one or both of the primers used for amplification can be attached to a gel material. Formats that utilize two species of attached primer are often referred to as bridge amplification because double stranded amplicons form a bridge-like structure between the two attached primers that flank the template sequence that has been copied. Exemplary reagents and conditions that can be used for bridge amplification are described, for example, in U.S. Pat. No. 5,641,658; U.S. Patent Publ. No. 2002/0055100; U.S. Pat. No. 7,115,400; U.S. Patent Publ. No. 2004/0096853; U.S. Patent Publ. No. 2004/0002090; U.S. Patent Publ. No. 2007/0128624; and U.S. Patent Publ. No. 2008/0009420, each of which is incorporated herein by reference. PCR amplification can also be carried out with one of the amplification primers attached to a gel material and the second primer in solution. An exemplary format that uses a combination of one solid phase-attached primer and a solution phase primer is emulsion PCR as described, for example, in Dressman et al., *Proc. Natl. Acad. Sci. USA* 100:8817-8822 (2003), WO 05/010145, or U.S. Patent Publ. Nos. 2005/0130173 or 2005/0064460, each of which is incorporated herein by reference. Emulsion PCR is illustrative of the format and it will be understood that for purposes of the methods set forth herein the use of an emulsion is optional and indeed for several embodiments an emulsion is not used. Furthermore, primers need not be attached directly to solid supports as set forth in the ePCR references and can instead be attached to a gel material as set forth herein. In some solid phase PCR or bridge amplification formats, a target nucleic acid can be attached to a gel material and used as a template for amplification.

RCA techniques can be modified for use in a method of the present disclosure. Exemplary components that can be used in an RCA reaction and principles by which RCA produces amplicons are described, for example, in Lizardi et al., *Nat. Genet.* 19:225-232 (1998) and US Pat. App. Pub. No. 2007/0099208 A1, each of which is incorporated herein by reference. Primers used for RCA can be in solution or attached to a gel material.

MDA techniques can be modified for use in a method of the present disclosure. Some basic principles and useful conditions for MDA are described, for example, in Dean et al., *Proc Natl. Acad. Sci. USA* 99:5261-66 (2002); Lage et al., *Genome Research* 13:294-307 (2003); Walker et al., Molecular Methods for Virus Detection, Academic Press, Inc., 1995; Walker et al., *Nucl. Acids Res.* 20:1691-96 (1992); U.S. Pat. Nos. 5,455,166; 5,130,238; and 6,214,587, each of which is incorporated herein by reference. Primers used for MDA can be in solution or attached to a gel material.

In particular embodiments a combination of the above-exemplified amplification techniques can be used. For example, RCA and MDA can be used in a combination wherein RCA is used to generate a concatameric amplicon in solution (e.g. using solution-phase primers). The amplicon can then be used as a template for MDA using primers that are attached to a gel material. In this example, amplicons produced after the combined RCA and MDA steps will be attached to the gel material. The amplicons will generally contain concatameric repeats of a target nucleotide sequence.

Amplification techniques, such as those exemplified above, can be used to produce gel-containing features having multiple copies of target nucleic acids. An individual feature, such as a well, can have a clonal population of nucleotide sequences in the form of a single molecule concatamer, such as those produced by RCA, or in the form of many nucleic acid molecules having the same sequence such as those produced by bridge PCR. Generally the nucleic acid(s) having several copies of the amplified target will be attached to the gel material.

For some applications, an individual gel-containing well (or other concave feature) can be predominantly populated with amplicons from a first target nucleic acid and can also have a low level of contaminating amplicons from a second target nucleic acid or from a spontaneous mutation occurring during amplification. An array can have one or more amplification sites that have a sufficiently low level of contaminating amplicons so as to have an unacceptable impact on a subsequent use of the array. For example, when the array is to be used in a detection application, an acceptable level of contamination would be a level that does not impact signal to noise or resolution of the detection technique in an unacceptable way. Accordingly, apparent clonality will generally be relevant to a particular use or application of an array made by the methods set forth herein. Exemplary levels of contamination that can be acceptable at an individual well or other feature for particular applications include, but are not limited to, at most 0.1%, 0.5%, 1%, 5%, 10% or 25% contaminating amplicons. An array can include one or more wells or other features having these exemplary levels of contaminating amplicons. For example, up to 5%, 10%, 25%, 50%, 75%, or even 100% of the features in an array can have some contaminating amplicons.

A gel material that has been coated on the surface of a solid support can be covalently attached to the support. As set forth above, the step of attaching an analyte, such as a nucleic acid, to gel material can be carried out at a variety of different stages in the manufacture of a structured substrate. Thus, a gel material can be attached to a solid support before or after attaching an analyte to the gel material. Attachment of gel material to a solid support can be carried out using any useful chemistry including without limitation those set forth in U.S. Prov. Pat. App. Ser. No. 61/753,833, which is incorporated herein by reference, or demonstrated in Example III below. It will be understood that covalent attachment of gel material to a solid support is not necessary in all embodiments. Thus, the subsequent steps of polishing a gel-coated support or using a polished substrate can be carried out for a substrate having gel material that is optionally, but not necessarily, covalently attached to concave features, such as wells.

A method set forth herein can include a step of removing gel material from the surface of a solid support. Gel material that is coated on a solid support can be selectively removed from interstitial regions using any of a variety of techniques. For example, gel material can be removed from a solid support having concave features and interstitial regions by a mechanical polishing technique. Mechanical polishing can be carried out by applying abrasive forces to the surface of the solid support. Exemplary methods include abrasion with a slurry of beads, wiping with a sheet or cloth, scraping or the like. It will be understood that beads used for polishing or other uses set forth herein can be, but need not be, spherical. Rather beads can have irregular shapes, polygonal shapes, ovoid shapes, elongated shapes, cylindrical shapes etc. The surface of the beads can be smooth or rough. Any of a variety of particles can be useful as beads for the methods and compositions set forth herein. One example of polishing includes using a lintless (cleanroom grade) wipe coated with a 3 μm silica bead slurry (10% w/v in water) to remove interstitial gel. A polishing wheel/grinder can also be used with this slurry. Mechanical polishing can also be achieved using a fluid jet or gas (e.g. air or inert gas such as Argon or Nitrogen) jet to remove gel from interstitial regions.

Polishing can involve chemical polishing such as hydrolysis or radical-based degradation of acrylamide (e.g. via exposure to benzoyl peroxide or dilute hydrogen peroxide as described in Kurenkov, et al., *Russian Journal of Applied Chemistry,* 75:1039-1050 (2002); Caulfield et al., *Polym.* 44:1331-1337 (2003); and Caulfield, et al., *Chem. Rev.* 102:3067-3083 (2002). During polishing, chemicals can be provided in a solid, liquid, gas or plasma state. Accordingly, plasma polishing can be useful in some embodiments.

Polishing can also involve a combination of chemical and mechanical polishing methods where a chemical slurry containing a colloidal suspension of particles is used to mechanically exfoliate and then chemically dissolve displaced portions of gel material from interstitial regions. Other methods to polish or clean the interstitial regions include adhesive based techniques, for example, techniques wherein a rigid, planar adhesive film with affinity to the gel material is coated on the surface thereby making intimate contact (e.g. via chemical linkage) with the gel material in interstitial regions. The mechanical removal/peeling of this adhesive film will result in the mechanical removal of the gel material from interstitial regions, while leaving gel material in concave features.

In another example, thiophosphate-grafted SFA can be removed from interstitial regions on a surface as follows. A water-dampened Whatman wipe can be dabbed into Aluminium oxide (~100 mg, 0.3 um) or steel beads. Then, the formed slurry can be rubbed on the surface of a solid support, in small concentric circles, using even pressure. A clean water-wet Whatman wipe can then be used to remove the slurry on the surface. The mechanical and chemical polishing methods exemplified herein for removing gel material from interstitial regions can also be used to inactivate gel material at interstitial regions, whether or not the gel material is removed. For example, the gel material can be inactivated with respect to the ability to attach to analytes such as nucleic acids or with respect to the ability to support nucleic acid amplification.

A method of making an array can include the steps of (a) providing a solid support having a surface with a plurality of wells, the wells containing a gel material, the wells being separated from each other by interstitial regions on the surface, the interstitial regions segregating the gel material in each of the wells from the gel material in other wells of the plurality; (b) delivering a library of target nucleic acids to the wells of the solid support to produce an array of wells that have a single species of target nucleic acid attached to the gel material in each well, wherein different wells in the array have different target nucleic acid species from the library; and (c) amplifying the target nucleic acids attached to the gel material in the wells of the array to produce a clonal population of an individual target nucleic acid at each of the wells of the array.

In several embodiments, the structured substrates set forth herein provide the advantage of convenient delivery of multiple different analytes from a mixture to individualized locations on the substrate, thereby forming an array. The structured substrates facilitate selective capture of a single analyte at each individual gel-containing well (or other concave feature) from a mixture of analytes in contact with the substrate. The pattern of gel-containing wells (or other concave features) on the structured substrate and the efficiency of loading can be adjusted to obtain arrays having desired characteristics such as analyte density and purity of each feature with respect to having a single analyte species. For example, a higher density of wells can be used to obtain a higher density of analytes on the array and, conversely a lower density of wells can be used to obtain a lower density of analytes on the array. Alternatively or additionally, the concentration or amount of analyte in solution can be increased to obtain a higher density of analytes on the array or decreased to obtain a lower density of analytes on the array. The average purity of analytes at each gel-containing well (or other concave feature) can be adjusted by altering properties of the substrate or conditions for delivery of analyte as set forth in further detail below and demonstrated in the Examples section.

In particular embodiments, the size or volume of the wells (or other concave features) can be adjusted to influence the purity of analytes captured. For example, a well can have an area or volume of gel material that accommodates only a single analyte of a particular type such that steric exclusion prevents more than one analyte molecule from being captured or seeding the well. Steric exclusion can be particularly useful for large analytes such as nucleic acids. More specifically, wells (or other concave features) can present a gel surface having an area that is equivalent to or smaller than the diameter of the excluded volume of the target nucleic acids that are to be seeded on the substrate. The excluded volume for a target nucleic acid and its diameter can be determined, for example, from the length of the target nucleic acid. Methods for determining the excluded volume of nucleic acids and the diameter of the excluded volume are described, for example, in U.S. Pat. No. 7,785,790; Rybenkov et al., *Proc. Natl. Acad. Sci. U.S.A.* 90: 5307-5311 (1993); Zimmerman et al., *J. Mol. Biol.* 222:599-620 (1991); or Sobel et al., *Biopolymers* 31:1559-1564 (1991), each of which is incorporated herein by reference. Conditions for steric exclusion are set forth in U.S. Ser. No. 13/661,524 and U.S. Pat. No. 7,785,790, each of which is incorporated herein by reference, and can be readily used for structured substrates of the present disclosure.

It will be understood that in some embodiments, wells (or other concave features) can present a gel surface having an area that is substantially greater than the diameter of the excluded volume of the target nucleic acids that are transported to the amplification sites. Thus, the area for the features can be sufficiently large that steric exclusion does not occur.

In some embodiments, such as the steric exclusion embodiments set forth above, a library of target nucleic acids can be delivered to gel-containing wells (or other concave features) of a solid support prior to initiation of an amplification process. For example, target nucleic acids can be delivered to a structured substrate under conditions to seed the gel material in the substrate with the target nucleic acids. The substrate can optionally be washed to remove target nucleic acids that do not seed the gel as well as any other materials that are unwanted for subsequent processing or use of the substrate. Amplification can include one or more of the techniques set forth previously herein.

In alternative embodiments, a library of target nucleic acids can be delivered to gel-containing wells (or other concave features) of a solid support and an amplification process can occur simultaneously with the seeding event. For example, seeding can occur under a regime that exploits kinetic exclusion as described for example in U.S. Ser. No. 61/715,478, which is incorporated herein by reference. Kinetic exclusion can occur when a process occurs at a sufficiently rapid rate to effectively exclude another event or process from occurring. In the case of an array of gel-containing wells, the wells can be randomly seeded with target nucleic acids from a solution and copies of the target nucleic acid can be generated in an amplification process to fill each of the seeded sites to capacity. The seeding and amplification processes can proceed simultaneously under conditions where the amplification rate exceeds the seeding rate. As such, the relatively rapid rate at which copies are made at a site that has been seeded by a first target nucleic acid will effectively exclude a second nucleic acid from seeding the site for amplification. Similarly, kinetic exclusion can exploit a relatively slow rate for making a first copy of a target nucleic acid vs. a relatively rapid rate for making subsequent copies of the target nucleic acid or of the first copy. For example, kinetic exclusion can occur due to a delay in the formation of a first copy of a target nucleic acid that has seeded a gel-containing well (e.g. delayed or slow activation) vs. the relatively rapid rate at which subsequent copies are made to fill the site. In this example, an individual gel-containing well may have been seeded with several different target nucleic acids (e.g. several target nucleic acids can be present at each site prior to amplification). However, first copy formation for any given target nucleic acid can be activated randomly such that the average rate of first copy formation is relatively slow compared to the rate at which subsequent copies are generated. In this case, although an individual gel-containing well may have been seeded with several different target nucleic acids, kinetic exclusion will allow only one of those target nucleic acids to be amplified. Generally, a gel-containing well (or other concave feature) can serve as a site for amplification and array formation in a method set forth in U.S. Ser. No. 61/715,478, which is incorporated herein by reference.

As an alternative to delivery of multiple different analytes from a mixture to individual gel-containing concave features, analytes can be discretely delivered to individual features from pure stocks. Similarly, analytes can be synthesized at individual features by discrete delivery of synthetic building blocks (e.g. nucleotide precursors can be sequentially delivered to synthesize nucleic acids). Exemplary methods for delivery of pure analytes or building blocks for synthesizing analytes in situ include, but are not limited to, ink jet array spotting and photolithographic array synthesis. Useful photolithographic methods include those used commercially by Affymetrix (Santa Clara, Calif.) to manufacture GeneChip® microarrays or described in U.S. Pat. Nos. 5,324,633; 5,744,305; 5,624,711; 6,022,963; 6,291,183; and 6,416,949, each of which is hereby incorporated by reference. Also useful are inkjet spotting techniques such as those commercialized by Agilent (Santa Clara, Calif.) for printing SurePrint™ arrays or described in U.S. Pat. No. 6,337,393; 6,419,883; 6,420,180 or 6,689,319, each of which is incorporated herein by reference. Such methods can be readily modified to direct delivery to gel-containing features of the present disclosure.

The gel material in a particular concave feature need not contain only a single species of analyte. Rather, in some embodiments a concave feature can contain several different species of analyte in the gel therein. An example is demonstrated by the bulls-eye fiducial markers in FIG. 5A and FIG. 5B. The fiducial markers include two 'bright' ring shaped channels, each of the two channels contains gel material, and the gel material in each bright channel is attached to a plurality of different nucleic acid colonies. The nucleic acid colonies in the bright channels were formed by seeding of each ring with several different species of target nucleic acid that functioned as templates in an amplification procedure. The fiducial marker also includes two 'dark' ring shaped regions. The dark rings are formed by interstitial surface patterns. The exemplary bulls-eye is formed by alternating dark and bright rings in a concentric pattern. In the example of FIG. 5A and FIG. 5B the structured substrate also includes gel-containing wells that each generally contains a clonal population derived from a single nucleic acid target. The wells occur in a ring shaped band between the bright and dark rings. Thus, the fiducials have an alternating pattern of interstitial ring, well-containing band and channel ring.

The same amplification procedure was used to simultaneously grow the clonal nucleic acid colonies in the wells and the mixed population in the fiducial marker (see Example III, below). Other examples of fiducials having alternating patterns of rings are shown in FIG. 3B and FIG. 3C.

This disclosure further provides a method of detecting analytes. The method can include the steps of (a) providing a solid support having a planar surface, wherein the planar surface is interrupted by one or more concave features, wherein the concave features contain gel material, wherein the one or more concave features are bordered by one or more interstitial regions on the planar surface, the interstitial regions being substantially devoid of the gel material, and wherein the gel material is attached to or contains target analytes; (b) contacting the solid support with probes under conditions wherein the target analytes interact specifically with the probes; and (c) detecting the solid support to distinguish at least a subset of the target analytes that interact with one or more of the probes.

In particular embodiments nucleic acids are the analytes that are detected and the concave features are wells. For example a method of detecting nucleic acids can include the steps of (a) providing a solid support having a surface and a library of nucleic acids, the surface having a plurality of wells, the wells containing a gel material, the wells being separated from each other by interstitial regions on the surface, the interstitial regions segregating the gel material in each of the wells from the gel material in other wells of the plurality, a single species of the target nucleic acids of the library being attached to the gel material in each of the wells; (b) contacting the solid support with at least one probe that binds to the target nucleic acids; and (c) detecting the solid support to distinguish the wells having a target nucleic acid species that binds to the at least one probe.

Structured substrates of the present disclosure that contain nucleic acid arrays can be used for any of a variety of purposes. A particularly desirable use for the nucleic acids is to serve as capture probes that hybridize to target nucleic acids having complementary sequences. The target nucleic acids once hybridized to the capture probes can be detected, for example, via a label recruited to the capture probe. Methods for detection of target nucleic acids via hybridization to capture probes are known in the art and include, for example, those described in U.S. Pat. No. 7,582,420; 6,890,741; 6,913,884 or 6,355,431 or US Pat. App. Pub. Nos. 2005/0053980 A1; 2009/0186349 A1 or 2005/0181440 A1, each of which is incorporated herein by reference. For example, a label can be recruited to a capture probe by virtue of hybridization of the capture probe to a target probe that bears the label. In another example, a label can be recruited to a capture probe by hybridizing a target probe to the capture probe such that the capture probe can be extended by ligation to a labeled oligonucleotide (e.g. via ligase activity) or by addition of a labeled nucleotide (e.g. via polymerase activity).

A nucleic acid array can also be used in a sequencing procedure, such as a sequencing-by-synthesis (SBS) technique. Briefly, SBS can be initiated by contacting the target nucleic acids with one or more labeled nucleotides, DNA polymerase, etc. Those features where a primer is extended using the target nucleic acid as template will incorporate a labeled nucleotide that can be detected. Optionally, the labeled nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the flow cell (before or after detection occurs). Washes can be carried out between the various delivery steps. The cycle can then be repeated n times to extend the primer by n nucleotides, thereby detecting a sequence of length n. Exemplary SBS procedures, fluidic systems and detection platforms that can be readily adapted for use with an array produced by the methods of the present disclosure are described, for example, in Bentley et al., *Nature* 456:53-59 (2008), WO 04/018497; WO 91/06678; WO 07/123744; U.S. Pat. No. 7,057,026; 7,329,492; 7,211,414; 7,315,019 or 7,405,281, and US Pat. App. Pub. No. 2008/0108082 A1, each of which is incorporated herein by reference.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., *Analytical Biochemistry* 242 (1), 84-9 (1996); Ronaghi, *Genome Res.* 11 (1), 3-11 (2001); Ronaghi et al. *Science* 281 (5375), 363 (1998); U.S. Pat. Nos. 6,210,891; 6,258,568 and 6,274,320, each of which is incorporated herein by reference). In pyrosequencing, released PPi can be detected by being converted to adenosine triphosphate (ATP) by ATP sulfurylase, and the resulting ATP can be detected via luciferase-produced photons. Thus, the sequencing reaction can be monitored via a luminescence detection system. Excitation radiation sources used for fluorescence based detection systems are not necessary for pyrosequencing procedures. Useful fluidic systems, detectors and procedures that can be used for application of pyrosequencing to arrays of the present disclosure are described, for example, in WIPO Pat. App. Ser. No. PCT/US11/57111, US Pat. App. Pub. No. 2005/0191698 A1, U.S. Pat. No. 7,595,883, and U.S. Pat. No. 7,244,559, each of which is incorporated herein by reference.

Sequencing-by-ligation reactions are also useful including, for example, those described in Shendure et al. *Science* 309:1728-1732 (2005); U.S. Pat. No. 5,599,675; and U.S. Pat. No. 5,750,341, each of which is incorporated herein by reference. Some embodiments can include sequencing-by-hybridization procedures as described, for example, in Bains et al., *Journal of Theoretical Biology* 135 (3), 303-7 (1988); Drmanac et al., *Nature Biotechnology* 16, 54-58 (1998); Fodor et al., *Science* 251 (4995), 767-773 (1995); and WO 1989/10977, each of which is incorporated herein by reference. In both sequencing-by-ligation and sequencing-by-hybridization procedures, nucleic acids that are present in gel-containing wells (or other concave features) are subjected to repeated cycles of oligonucleotide delivery and detection. Fluidic systems for SBS methods as set forth herein, or in references cited herein, can be readily adapted for delivery of reagents for sequencing-by-ligation or sequencing-by-hybridization procedures. Typically, the oligonucleotides are fluorescently labeled and can be detected using fluorescence detectors similar to those described with regard to SBS procedures herein or in references cited herein.

Some embodiments can utilize methods involving the real-time monitoring of DNA polymerase activity. For example, nucleotide incorporations can be detected through fluorescence resonance energy transfer (FRET) interactions between a fluorophore-bearing polymerase and γ-phosphate-labeled nucleotides, or with zeromode waveguides. Techniques and reagents for FRET-based sequencing are described, for example, in Levene et al. *Science* 299, 682-

686 (2003); Lundquist et al. *Opt. Lett.* 33, 1026-1028 (2008); Korlach et al. *Proc. Natl. Acad. Sci.* USA 105, 1176-1181 (2008), the disclosures of which are incorporated herein by reference.

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in US Pat. App. Pub. Nos. 2009/0026082 A1; 2009/0127589 A1; 2010/0137143 A1; or 2010/0282617 A1, each of which is incorporated herein by reference. In particular embodiments, the electrical detectors that are used to detect the released protons can be modified to include wells and the wells can contain gel material as set forth herein.

Another useful application for an array of the present disclosure is gene expression analysis. Gene expression can be detected or quantified using RNA sequencing techniques, such as those, referred to as digital RNA sequencing. RNA sequencing techniques can be carried out using sequencing methodologies known in the art such as those set forth above. Gene expression can also be detected or quantified using hybridization techniques carried out by direct hybridization to an array or using a multiplex assay, the products of which are detected on an array. An array of the present disclosure can also be used to determine genotypes for a genomic DNA sample from one or more individual. Exemplary methods for array-based expression and genotyping analysis that can be carried out on an array of the present disclosure are described in U.S. Pat. No. 7,582,420; 6,890,741; 6,913,884 or 6,355,431 or US Pat. App. Pub. Nos. 2005/0053980 A1; 2009/0186349 A1 or 2005/0181440 A1, each of which is incorporated herein by reference.

Several applications for arrays of the present disclosure have been exemplified above in the context of ensemble detection, wherein multiple copies of a target nucleic acid are present at each feature and are detected together. In alternative embodiments, a single nucleic acid, whether a target nucleic acid or amplicon thereof, can be detected at each feature. For example, a gel-containing well (or other concave feature) can be configured to contain a single nucleic acid molecule having a target nucleotide sequence that is to be detected. Any of a variety of single molecule detection techniques can be used including, for example, modifications of the ensemble detection techniques set forth above to detect the sites at increased resolution or using more sensitive labels. Other examples of single molecule detection methods that can be used are set forth in US Pat. App. Pub. No. 2011/0312529 A1; U.S. Ser. No. 61/578,684; and U.S. Ser. No. 61/540,714, each of which is incorporated herein by reference.

It will be understood that a gel-containing substrate of the present disclosure, for example, having been produced by a method set forth herein, need not be used for a detection method. Rather, the structured substrate can be used to store a nucleic acid library. Accordingly, the structured substrate can be stored in a state that preserves the nucleic acids therein. For example, a substrate having gel-containing wells that are attached to nucleic acids can be stored in a desiccated state, frozen state (e.g. in liquid nitrogen), or in a solution that is protective of nucleic acids. Alternatively or additionally, the structured substrate can be used to replicate a nucleic acid library. For example, a substrate having gel-containing wells that are attached to nucleic acids can be used to create replicate amplicons from one or more of the wells on the array.

The following examples are intended to illustrate but not limit the present invention.

EXAMPLE I

Multiwell Substrates Coated with Silane Free Acrylamide

This example demonstrates coating of nanowell substrates with silane free acrylamide (SFA), followed by grafting with thiophosphate primers and performing a hybridization of the gel-grafted primers to complimentary fluorescent oligonucleotide to confirm the success of the functionalization approach.

Chip substrates normally used for manufacture of Bead-Chips were obtained from Illumina (San Diego, Calif.). The chips were made of silicon or Zeonor (Zeon Corp., Tokyo, Japan) having 0.5 μm wells arranged in a hexagonal pattern having a pitch of 1.5 μm, but the wells did not contain beads beads. The chips were patterned with gel pads as set forth below and diagrammed in FIG. 1.

The chips were encased in a gasket sealed chamber and oxygen was removed by displacement with fluid reagents for formation of SFA. SFA was polymerized on the chips in the chamber. The reagents for formation of SFA and conditions for polymerization were otherwise as described in US Pat. App. Pub. No. 2011/0059865 A1, which is incorporated herein by reference. The sealed chamber was used to place the polymerizing mix in direct contact with the chip and to ensure complete elimination of air since free radical polymerization of SFA is an air-sensitive process. After polymerization, primers were grafted to the SFA polymer in the sealed chamber as set forth in US Pat. App. Pub. No. 2011/0059865 A1 and as follows. A solution containing the primers was drawn across the polymer coated surface of the BeadChip and the mix was then incubated for 1.25 h at 65° C. (the entire sealed assembly was placed in a large oven).

Figure 2A:
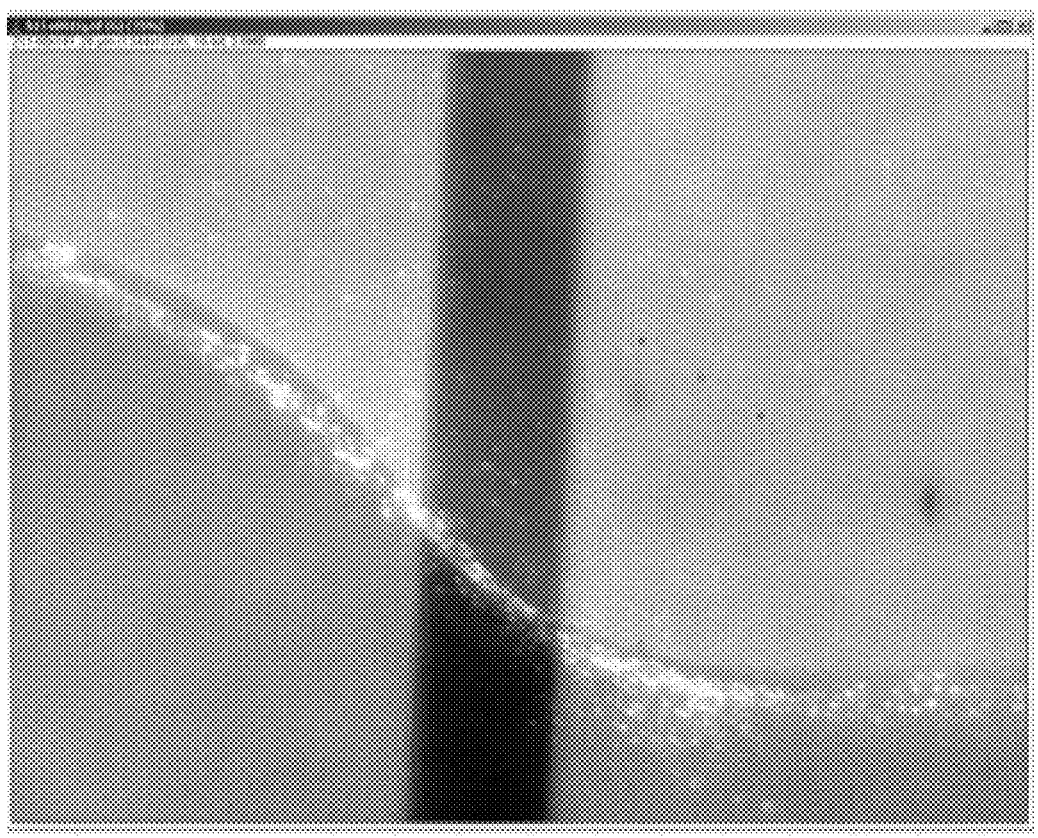
FIG. 2A, FIG. 2B and FIG. 2C show images from a BeadChip substrate modified to have gel material in the wells instead of beads.
Figure 2B:
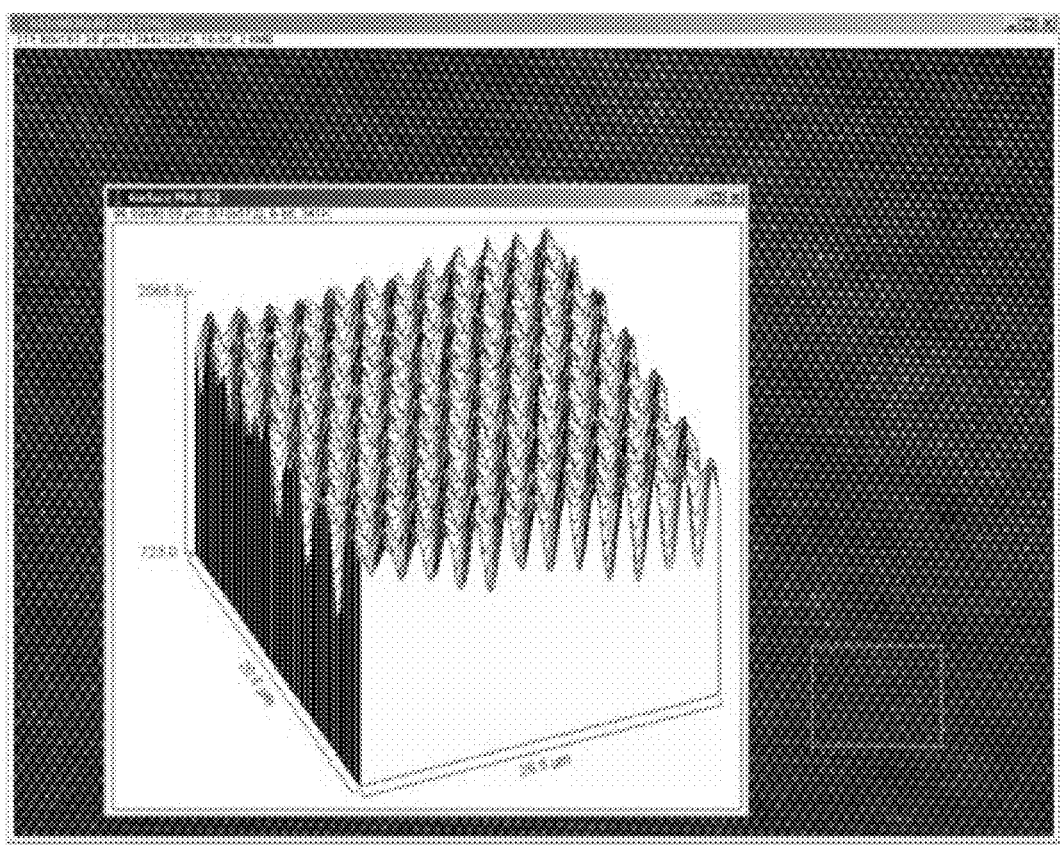
Figure 2C:
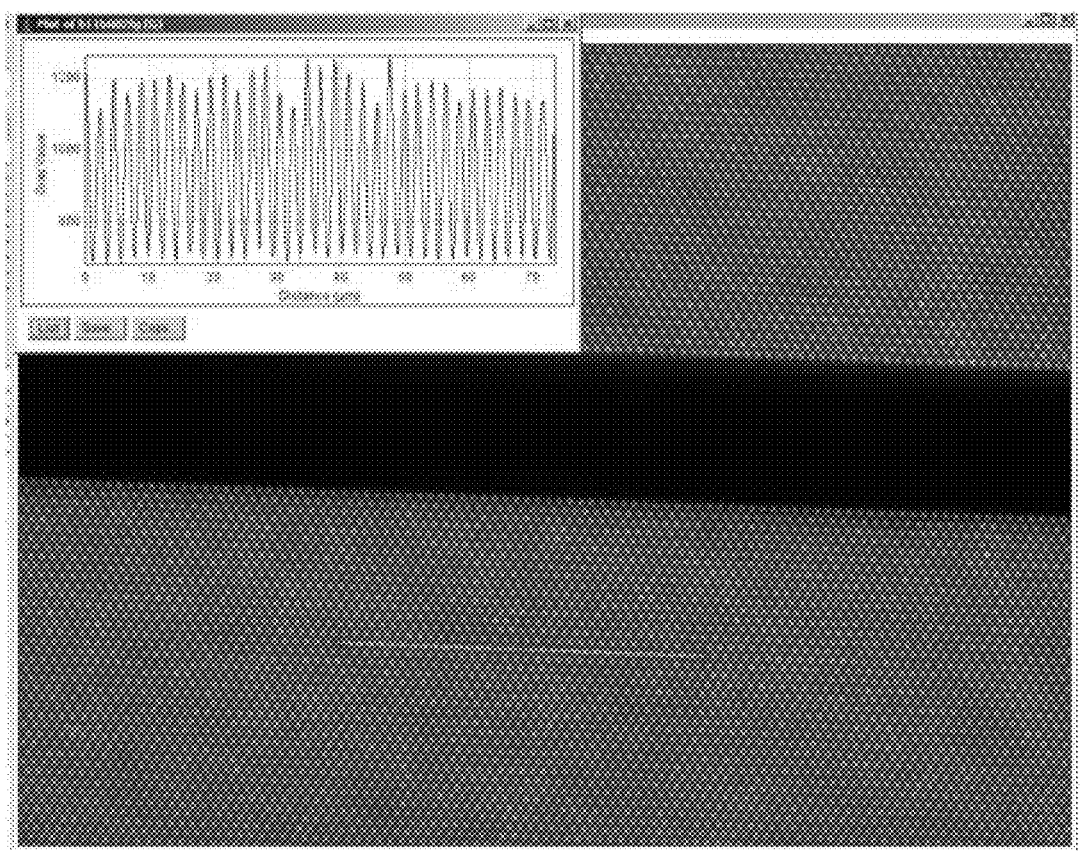

This approach gave uniformly coated substrates. A sample image is shown in FIG. 2A. In order to create discrete polymer regions, the 'excess' polymer situated between the wells on the substrate was removed using a mechanical polishing technique using a slurry of aluminum oxide nanoparticles (300 nm diameter) in DI water. A 10 wt. % slurry of 3 micron silica particles (Kisker Biotech GmbH, Steinfurt, Germany) can also be used. The surface was manually scrubbed with the nanoparticle slurry using a lint-free optical tissue. After washing to remove the slurry and polymer debris, a solution of fluorescently labeled probes was hybridized to the chip. Images captured using a fluorescence microscope showed that this approach was capable of yielding polymer features with clean interstitial regions (FIG. 2B through FIG. 2C).

These results indicated that the fluorescent intensities at the gel-filled wells were spatially discrete in contrast to the absence of signal from the interstitial regions. The results also demonstrated that gel patterning can be achieved using non-covalently attached gel material on a substrate having nanofabricated wells.

EXAMPLE II

Fabrication of a Substrate Having Gel-Containing Nanowells

Multiple techniques can be used to fabricate structured arrays that can subsequently be loaded with gel material.

The process can start with a blank substrate/wafer and a pattern is introduced into the substrate via micro- or nano-fabrication techniques. The material of the substrate/wafer can be conventional silicon, glass, plastic, COC or any of a variety of materials that can be structured. Exemplary techniques for introducing the patterning into the substrate include photolithography, nanoimprint lithography, embossing of the structures into a plastic/COC based material and injection molding of a plastic or COC into a master mold that has the structures patterned into it. Photolithography based approaches will typically involve use of a photoresist that is patterned with a stepper or mask aligner, exposed with radiation which transfers the pattern present on a reticle/photomask into the photoresist, and then the resist is developed to yield a structured film (photoresist) on top of the substrate. The structured resist is potentially the final substrate which can be used for subsequent gel coating or the pattern in the resist can be transferred into the substrate via follow on processing. The follow on process steps will typically include reactive ion etching (plasma based etching) or a wet etch (chemically based) process. If the pattern is transferred into the substrate, the patterned photoresist is subsequently removed to yield the patterned substrate for subsequent gel coating. It may be desirable to use a sacrificial film of a material such as Chrome or Titanium (a metal) under the photoresist, and first transfer the pattern in the photoresist to the metal film and then use that film as a hard mask by which the pattern is transferred into the substrate. Following pattern transfer into the substrate, the films are removed and therefore considered sacrificial to the fabrication process. If nanoimprint lithography is used, the imprinted photoresist can be a sacrificial material and similarly be used as an intermediate tool to transfer the patterned resist into the substrate or a variation of the resist can be used such that the imprinted resist serves as the input to a subsequent coating step. An example of a resist that would remain following patterning would be a Sol-Gel based material.

A diagrammatic representation of how a structured substrate may be fabricated is shown in FIG. 3A and described below. Images of patterned substrates are shown at various magnification levels in FIG. 3B and FIG. 3C.

Creation of chemically specific gel pads on a sequencing substrate/flowcell can involve one or more of the nanofabrication techniques set forth previously in this Example. The process may optionally then include one or more chemical processing steps, such as silanization to allow subsequent linking of a gel polymer to the substrate via the silane. Then chemical/mechanical polishing (CMP) is used to remove all interstitial polymer on the surface of the substrate. The polishing process will remove material in a top down fashion and since the structured features in the substrate are effectively offset from the plain of the interstitial regions of the array, the polishing will remove the polymer from the interstitial prior to removing the structured features. If the polishing process is stopped after the optimum time, the structures will retain the polymer coating and the interstitial regions will be void of the polymer. The patterned gel pad substrate is then grafted with primers, target nucleic acids are seeded at the gel pads and the target nucleic acids are used as templates for creation of nucleic acid clusters at the gel pads.

EXAMPLE III

Multiwell Substrates Coated with PAZAM

This example shows the fabrication of an array of gel-containing wells, amplification of nucleic acid clusters in the wells and sequencing of the nucleic acids in the clusters.

Substrates were fabricated as follows. A nanowell substrate (400 nm diameter 1.5 µm pitch, 300 nm depth well) was fabricated using nanoimprint lithography. An amino silane (APTES or APTMS) monolayer/multilayer was deposited on the entire surface of the substrate using chemical vapor deposition. Next, a 1× phosphate buffered saline (pH 7.4) solution of acrylic acid N-hydroxysuccinimide ester (Aldrich PN 8060) at 100 mM concentration was reacted with the amino silane surface by adding 1 ml of the NHS acrylate solution to the surface, covering it with a thin glass coverslip and allowing the reaction to proceed for 1 hour at room temperature. A polymer (PAZAM) was then applied to the surface by spin coating 500 µl of a 2 wt. % PAZAM solution in water onto the newly formed acrylamide functionalized surface. PAZAM was synthesized as described in U.S. Prov. Pat. App. Ser. No. 61/753,833, which is incorporated herein by reference. Subsequent heating of the PAZAM-coated substrate at 60° C. for 1 hour resulted in a covalent linkage between the polymer and surface. The interstitial covalently linked polymer was removed by polishing the surface with 10 wt. % of 3 µm $SiO_2$ micro particle slurry in water. A Janeway surface (acryloyl chloride with DIPEA in MeCN) can be used in place of the amino silane coated surface in the above procedure.

Figure 4:
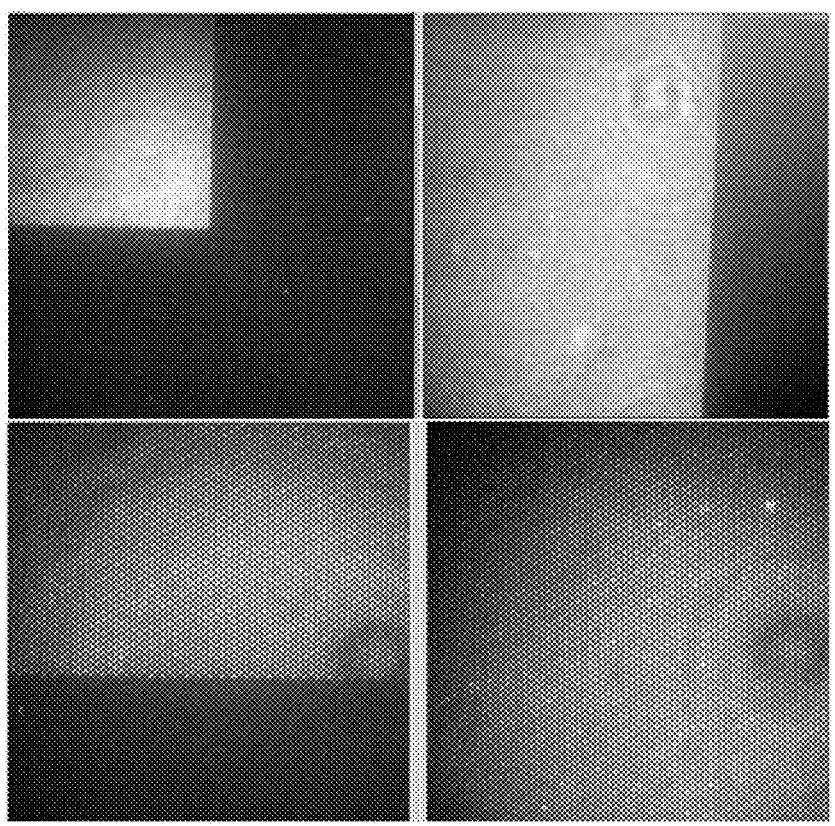
FIG. 4 shows high resolution fluorescence microscope images of nanowell substrates showing patterned gel features on the nanowell substrate after the substrate is coated with PAZAM and polished with a silica bead slurry. The PAZAM is labeled with a dye for visualization purposes.
Figure 6A:
FIG. 6A shows a multi-color merge of patterned clusters in a Hiseq sequencing run with a 750 nm pitch nanowell substrate.
Figures 6B, 6C:
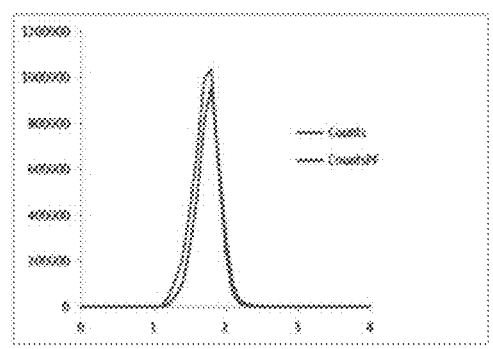
FIG. 6B shows nearest neighbor curve showing the array is ordered and clusters are passing quality filters.
FIG. 6C shows sequencing quality metrics showing that at a density of 1.6 million clusters/mm$^2$ quality filters were successfully passed.

The patterned polymer substrate was then grafted with primers as described in U.S. Prov. Pat. App. Ser. No. 61/753,833, which is incorporated herein by reference. Next, dye-labeled (Cy5) reverse compliments of the grafted primers were exposed to the surface in a 1×PBS buffer solution at a compliment concentration of 20 µM, and then the surface was washed with 50 ml of 1 PBS buffer applied with a squirt bottle. The labeled complements on the substrate were imaged with a FLA 9500Typhoon Imager set at the Cy5 scan channel and using a PMT setting of 450. The labeled compliments on the substrate were also imaged with a high resolution microscope, showing the patterning or polymer/primers with no interstitial polymer/primers remaining (FIG. 4). The substrate was then seeded with phiX DNA, and clusters grown as described in U.S. Ser. No. 61/715,478, which is incorporated herein by reference.

Figure 7:
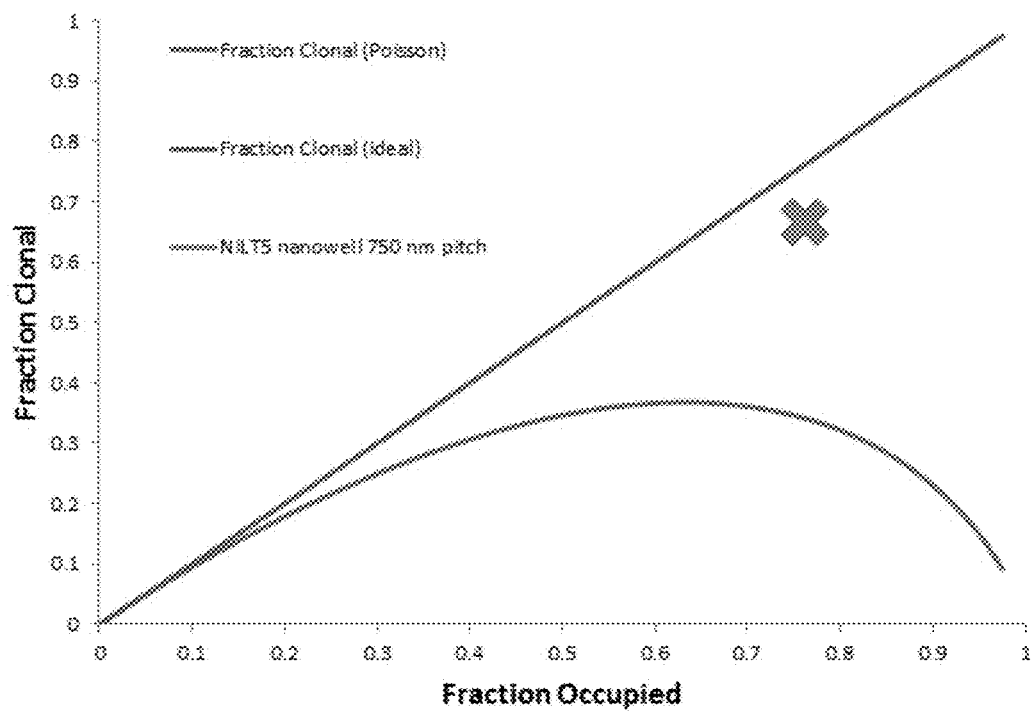
FIG. 7 is a plot of Fraction clonal vs. Fraction occupied with the curve expected for a Poisson distribution, a straight line expected for ideal clonality and occupancy and an X for the average measure obtained from a sequencing run with a substrate having a pattern of gel-containing nanowells.

A flow cell containing the cluster-containing substrate was sequenced on a HiSeq 2000 (Illumina, Inc., San Diego, Calif.). An algorithm to extract the locations of the patterned sequencing clusters (rigid registration) was employed, successfully giving high quality sequencing metrics (FIG. 5A, FIG. 5B, FIG. 6A, FIG. 6B and FIG. 6C). Sequencing results showed that the occupancy vs. clonality was surprisingly higher than expected for a standard Poisson distribution. Specifically, the average occupancy vs. clonality measure for the sequencing run, as indicated by the "x" in FIG. 7, is above the boundaries of the Poisson curve and approaches closely to the line for the ideal clonal fraction).

Throughout this application various publications, patents or patent applications have been referenced. The disclosures of these publications in their entireties are hereby incorporated by reference in this application in order to more fully describe the state of the art to which this invention pertains.

The term "comprising" is intended herein to be open-ended, including not only the recited elements, but further encompassing any additional elements.

Although the invention has been described with reference to the examples provided above, it should be understood that various modifications can be made without departing from the invention. Accordingly, the invention is limited only by the claims.

What is claimed is:

1. An array, comprising
a solid support comprising a surface, the surface comprising a plurality of wells, the wells containing a gel material, the wells being separated from each other by interstitial regions on the surface, the interstitial regions segregating the gel material in each of the wells from the gel material in other wells of the plurality, wherein the volume of each of the wells is at most $1 \times 10^4$ $\mu m^3$; and
a library of target nucleic acids in the gel material, wherein the gel material in each of the wells comprises a different species of the target nucleic acids of the library compared to species of the target nucleic acids in other wells of the solid support, and wherein the gel material comprises poly(N-(5-azidoacetamidylpentyl)acrylamide-co-acrylamide).

2. The array of claim 1,
wherein the plurality of wells is in a flow cell that contains a solution and wherein the library of target nucleic acids that is in the plurality of wells has simultaneous fluidic access to the solution.

3. The array of claim 1, wherein the plurality of wells form an array having a repeating pattern.

4. The array of claim 3, wherein the wells in the pattern have a pitch of no more than 5 micrometers.

5. The array of claim 1, wherein the wells comprise a non-silanized surface.

6. The array of claim 1, wherein the gel material in each of the wells comprises multiple copies of a single species of target nucleic acid of the library.

7. The array of claim 6, wherein the multiple copies of the single species form a clonal population of nucleic acid molecules.

8. The array of claim 6, wherein the multiple copies of the single species are present as concatameric repeats in a nucleic acid molecule.

9. The array of claim 1, wherein the surface comprises a density of at least 1,000 of the wells per $mm^2$.

10. The array of claim 1, wherein the gel material is covalently attached to the surface of the wells.

11. The array of claim 1, wherein each of the wells comprises an opening in the surface that is at most 100 $\mu m^2$.

12. The array of claim 1, wherein a single species of a target nucleic acid of the library is present in each of the wells as no more than a single nucleic acid molecule.

13. The array of claim 12, wherein the single nucleic acid molecule comprises two complementary strands.

14. The array of claim 1, wherein the gel is non-covalently retained in the wells.

15. The array of claim 1, wherein the target nucleic acids are not attached to beads in the wells.

16. The array of claim 1, further comprising a concave feature that contains several different species of the target nucleic acids of the library.

17. The array of claim 16, wherein the concave feature comprises a fiducial.

18. The array of claim 16, wherein the concave feature is a well.

19. The array of claim 1, wherein the gel material in each of the wells fills part of the volume of the well where it resides.

20. A method of detecting nucleic acids, comprising
(a) providing the array of claim 2;
(b) contacting the solid support with at least one probe that binds to the target nucleic acids; and
(c) detecting the solid support to distinguish the wells having a target nucleic acid species that binds to the at least one probe.

21. The method of claim 20, wherein the at least one probe comprises at least one nucleic acid that is complementary to at least a portion of at least one of the target nucleic acids.

22. The method of claim 21, wherein the at least one probe further comprises a polymerase and a nucleotide.

23. The method of claim 20, wherein steps (b) and (c) are repeated several times in a sequencing procedure.

24. The method of claim 20, wherein the probe comprises a nucleic acid binding protein.

25. A method of detecting analytes, comprising
(a) providing the array of claim 2;
(b) contacting the solid support with probes under conditions wherein the target analytes interact specifically with the probes; and
(c) detecting the solid support to distinguish at least a subset of the target analytes that interact with one or more of the probes.

* * * * *